US009433880B2

(12) United States Patent
Lean et al.

(10) Patent No.: US 9,433,880 B2
(45) Date of Patent: Sep. 6, 2016

(54) PARTICLE SEPARATION AND CONCENTRATION SYSTEM

(75) Inventors: Meng H. Lean, Santa Clara, CA (US);
Jeonggi Seo, Albany, CA (US);
Ashutosh Kole, Sunnyvale, CA (US);
Norine E. Chang, Menlo Park, CA (US); Scott Jong Ho Limb, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 11/606,460

(22) Filed: Nov. 30, 2006

(65) Prior Publication Data

US 2008/0128331 A1 Jun. 5, 2008

(51) Int. Cl.
*B03B 5/00* (2006.01)
*B01D 21/26* (2006.01)
(Continued)

(52) U.S. Cl.
CPC .............. *B01D 21/265* (2013.01); *B03B 5/32* (2013.01); *B04C 1/00* (2013.01); *B01D 2221/10* (2013.01); *B01D 2311/04* (2013.01); *B01D 2311/16* (2013.01); *B01D 2321/2025* (2013.01); *G01N 15/0255* (2013.01); *G01N 15/04* (2013.01)

(58) Field of Classification Search
USPC .......... 209/155, 156, 18, 132, 142; 210/194, 210/255, 512.1, 779, 788
See application file for complete search history.

(56) References Cited

U.S. PATENT DOCUMENTS 1,133,721 A 3/1915 Gregg
1,836,758 A 12/1931 Knapp
(Continued)

FOREIGN PATENT DOCUMENTS

CN 1149556 5/1997
DE 2809630 9/1978
(Continued)

OTHER PUBLICATIONS

Yang et al., "Particle Separation in Microfluidic Channels Using Flow Rate Control," Proceedings of IMECE2004-60862, pp. 1-6, Anaheim, CA, Nov. 13-19, 2004.
(Continued)

*Primary Examiner* — Terrell Matthews
(74) *Attorney, Agent, or Firm* — Fay Sharpe LLP

(57) ABSTRACT

This invention is based on size and mass separation of suspended particles, including biological matter, which are made to flow in a spiral channel. On the spiral sections, the inward directed transverse pressure field from fluid shear competes with the outward directed centrifugal force to allow for separation of particles. At high velocity, centrifugal force dominates and particles move outward. At low velocities, transverse pressure dominates and the particles move inward. The magnitudes of the two opposing forces depend on flow velocity, particle size, radius of curvature of the spiral section, channel dimensions, and viscosity of the fluid. At the end of the spiral channel, a parallel array of outlets collects separated particles. For any particle size, the required channel dimension is determined by estimating the transit time to reach the side-wall. This time is a function of flow velocity, channel width, viscosity, and radius of curvature. Larger particles may reach the channel wall earlier than the smaller particles which need more time to reach the side wall. Thus a spiral channel may be envisioned by placing multiple outlets along the channel. This technique is inherently scalable over a large size range from sub-millimeter down to 1 μm.

34 Claims, 20 Drawing Sheets

(51) Int. Cl.
*B03B 5/32* (2006.01)
*B04C 1/00* (2006.01)
G01N 15/02 (2006.01)
G01N 15/04 (2006.01)

(56) References Cited

U.S. PATENT DOCUMENTS

| | | | |
|---|---|---|---|
| 2,426,804 A | | 9/1947 | Roy |
| 2,584,976 A | * | 2/1952 | Bailey, Jr. ............... B07B 7/08 209/459 |
| 2,615,572 A | | 10/1952 | Hodge |
| 3,225,523 A | * | 12/1965 | Wiebed ................. B01D 45/06 209/273 |
| 3,672,503 A | | 6/1972 | Mark |
| 3,693,791 A | | 9/1972 | Beck |
| 3,893,921 A | | 7/1975 | Walther et al. |
| 3,933,642 A | | 1/1976 | Wilson |
| 3,948,771 A | | 4/1976 | Bielefeldt |
| 4,001,121 A | | 1/1977 | Bielefeldt |
| 4,128,474 A | | 12/1978 | Ennis |
| 4,153,541 A | | 5/1979 | Rumpf et al. |
| 4,159,942 A | | 7/1979 | Greer et al. |
| 4,189,378 A | | 2/1980 | Wright et al. |
| 4,292,050 A | | 9/1981 | Linhardt et al. |
| 4,324,334 A | | 4/1982 | Wright et al. |
| 4,343,707 A | | 8/1982 | Lucas |
| 4,383,917 A | * | 5/1983 | Wells ........................... 209/723 |
| 4,386,519 A | | 6/1983 | Sinkey |
| 4,451,367 A | | 5/1984 | Ruggeri |
| 4,460,391 A | | 7/1984 | Muller et al. |
| 4,462,907 A | * | 7/1984 | Waldecker .......... B01D 21/0009 209/224 |
| 4,505,811 A | | 3/1985 | Griffiths et al. |
| 4,542,775 A | | 9/1985 | Beck |
| 4,789,476 A | * | 12/1988 | Schulz ........................... 55/460 |
| 4,795,553 A | | 1/1989 | Giffard |
| 4,872,972 A | * | 10/1989 | Wakabayashi et al. ...... 209/143 |
| 4,927,437 A | | 5/1990 | Richerson |
| 5,059,226 A | | 10/1991 | Schneider et al. |
| 5,104,520 A | | 4/1992 | Maronde et al. |
| 5,120,436 A | | 6/1992 | Reichner |
| 5,193,688 A | * | 3/1993 | Giddings ................... B03B 5/00 209/127.1 |
| 5,314,529 A | * | 5/1994 | Tilton et al. ..................... 96/204 |
| 5,535,892 A | | 7/1996 | Moorhead et al. |
| 5,556,537 A | | 9/1996 | Saarenketo |
| 5,587,128 A | | 12/1996 | Wilding et al. |
| 5,626,758 A | | 5/1997 | Belfort |
| 5,632,957 A | | 5/1997 | Heller et al. |
| 5,653,859 A | | 8/1997 | Parton et al. |
| 5,690,763 A | | 11/1997 | Ashmead et al. |
| 5,711,882 A | | 1/1998 | Hofmann et al. |
| 5,715,946 A | * | 2/1998 | Reichenbach ..... B01D 21/0009 209/156 |
| 5,728,262 A | | 3/1998 | Moss et al. |
| 5,866,000 A | * | 2/1999 | Yeh ..................... B01D 17/0217 210/295 |
| 5,958,240 A | | 9/1999 | Hoel |
| 5,971,158 A | | 10/1999 | Yager et al. |
| 5,993,668 A | | 11/1999 | Duan |
| 6,013,165 A | | 1/2000 | Wiktorowicz et al. |
| 6,087,608 A | | 7/2000 | Schlichter et al. |
| 6,100,535 A | | 8/2000 | Mathies et al. |
| 6,272,296 B1 | | 8/2001 | Gartstein |
| 6,355,491 B1 | | 3/2002 | Zhou et al. |
| 6,422,735 B1 | | 7/2002 | Lang |
| 6,454,945 B1 | | 9/2002 | Weigl et al. |
| 6,527,125 B2 | | 3/2003 | Niitti |
| 6,569,323 B1 | * | 5/2003 | Pribytkov .................... 210/181 |
| 6,811,713 B2 | * | 11/2004 | Arnaud ............. B01D 21/2433 209/715 |
| 6,824,679 B1 | | 11/2004 | Dzengeleski et al. |
| 6,827,911 B1 | | 12/2004 | Gering |
| 6,905,029 B2 | | 6/2005 | Flagan |
| 7,104,405 B2 | | 9/2006 | Bohm et al. |
| 7,156,970 B2 | | 1/2007 | Lean et al. |
| 7,163,611 B2 | | 1/2007 | Volkel et al. |
| 7,226,542 B2 | | 6/2007 | Zemel et al. |
| 7,241,423 B2 | | 7/2007 | Golbig et al. |
| 7,282,129 B2 | | 10/2007 | Lean et al. |
| 7,328,807 B2 | | 2/2008 | Takagi et al. |
| 7,431,228 B2 | * | 10/2008 | Bohm ................... A23L 1/1016 241/11 |
| 7,473,216 B2 | * | 1/2009 | Lolachi et al. ................ 494/45 |
| 7,491,307 B2 | | 2/2009 | Hsieh et al. |
| 7,497,334 B2 | | 3/2009 | Tyvoll et al. |
| 7,534,336 B2 | | 5/2009 | Volkel et al. |
| 7,584,857 B2 | | 9/2009 | Bohm et al. |
| 7,770,738 B2 | | 8/2010 | Tabata et al. |
| 8,869,987 B2 | * | 10/2014 | Lean ................... B01D 21/0087 209/155 |
| 2002/0130068 A1 | | 9/2002 | Fassbender et al. |
| 2003/0221996 A1 | * | 12/2003 | Svoronos ........... B01D 46/2403 209/1 |
| 2004/0038249 A1 | | 2/2004 | Darteil et al. |
| 2005/0183996 A1 | | 8/2005 | Zemel et al. |
| 2006/0040596 A1 | | 2/2006 | Robinson |
| 2006/0087918 A1 | * | 4/2006 | Ji ........................ B01F 5/0646 366/341 |
| 2006/0118479 A1 | | 6/2006 | Shevkoplyas et al. |
| 2006/0158640 A1 | | 7/2006 | Molter et al. |
| 2006/0240964 A1 | * | 10/2006 | Lolachi et al. ................ 494/37 |
| 2009/0014360 A1 | * | 1/2009 | Toner .................. B01D 21/0087 209/208 |
| 2009/0050538 A1 | * | 2/2009 | Lean et al. .................... 209/155 |
| 2009/0114601 A1 | | 5/2009 | Lean et al. |
| 2009/0114607 A1 | | 5/2009 | Lean et al. |
| 2009/0283452 A1 | | 11/2009 | Lean et al. |
| 2009/0283455 A1 | | 11/2009 | Lean et al. |

FOREIGN PATENT DOCUMENTS

| | | |
|---|---|---|
| DE | 2829592 | 1/1980 |
| DE | 29 29 139 A1 | 1/1981 |
| DE | 2929139 A1 | 1/1981 |
| DE | 3736504 | 3/1989 |
| DE | 4200802 | 7/1993 |
| DE | 19855256 | 6/2000 |
| DE | 10001737 | 10/2001 |
| DE | 102004039182 | 2/2006 |
| EP | 0448973 A | 10/1991 |
| EP | 0448973 A1 | 10/1991 |
| EP | 1407807 A | 4/2004 |
| EP | 1407807 A1 | 4/2004 |
| EP | 1 681 549 A2 | 7/2006 |
| EP | 1681549 A | 7/2006 |
| EP | 1 795 894 A1 | 6/2007 |
| EP | 1795894 A | 6/2007 |
| EP | 1942329 | 7/2008 |
| EP | 2060312 | 5/2009 |
| FR | 2571354 | 4/1986 |
| FR | 2753392 | 3/1998 |
| GB | 330163 | 6/1930 |
| GB | 386080 A | 1/1933 |
| GB | 934423 | 8/1963 |
| GB | 1039485 | 8/1966 |
| GB | 2012193 | 7/1979 |
| GB | 2024038 | 1/1980 |
| GB | 2098091 A | 11/1982 |
| GB | 2209969 | 6/1989 |
| JP | S56-80272 | 6/1981 |
| JP | 57-150161 | 9/1982 |
| JP | S57-150464 | 9/1982 |
| JP | 60071083 | 4/1985 |
| JP | S60-108329 | 7/1985 |
| JP | 63319017 | 12/1988 |
| JP | H02-86876 | 3/1990 |
| JP | 5007795 A | 1/1993 |
| JP | 2001121039 | 5/2001 |
| JP | 2003-126633 | 5/2003 |
| JP | 2003-126678 | 5/2003 |
| JP | 2004-330008 A | 11/2004 |
| JP | 2007069179 | 3/2007 |
| JP | 9299712 | 11/2007 |

(56) References Cited

FOREIGN PATENT DOCUMENTS

| JP | 045049795 B2 | 7/2010 |
|---|---|---|
| KR | 20030003206 | 1/2003 |
| WO | WO8603140 | 6/1986 |
| WO | WO8810239 | 12/1988 |
| WO | WO9838134 | 9/1998 |
| WO | WO 2004/113877 A1 | 12/2004 |
| WO | WO2004113877 | 12/2004 |
| WO | WO 2006/056219 A1 | 6/2006 |
| WO | WO2006056219 | 6/2006 |

OTHER PUBLICATIONS

Takagi et al., "Continuous Particle Separation in a Microchannel having Asymmetrically Arranged Multiple Branches,", Lab on a Chip 2005, Lab Chip, 2005, 5, pp. 778-784, May 19, 2005.
Zhang et al., "Continuous Flow Separation of Particles Within an Asymmetric Microfluidic Device," Lab on a Chip 2006, Lab Chip, 2006, 6, pp. 561-566, Mar. 13, 2006.
Narayanan et al., "A Microfabricated Electrical SPLITT System," Lab on a Chip 2006, Lab Chip, 2006, 6, pp. 105-114, Dec. 5, 2005.
Kapishnikov et al., "Continuous Particle Size Separation and Size Sorting Using Ultrasound in a Microchannel," Journal of Statistical Mechanics: Theory and Experiment, PO1012, pp. 1-15, 2006.
Brenner, "Polymer Fabrication and Microfluidic Unit Operations for Medical Diagnostics on a Rotating Disk," Dissertation at Institute of Microsystems, University of Frieburg, Dec. 2005.
Ookawara et al., "Feasibility Study on Concentration of Slurry and Classification of Contained Particles by Microchannel," Chemical Engineering Journal, v. 101, pp. 171-178, 2004.
Matthews et al., "Particle Flow Modelling on Spiral Concentrators: Benefits of Dense Media for Coal Processing?," Second International Conference on CFD in the Minerals and Process Industries, CSIRO, Melbourne, Australia, pp. 211-216, Dec. 6-8, 1999.
Shi et al., "Radial Capillary Array Electrophoresis Microplate and Scanner for High-Performance Nucleic Acid Analysis," Analytical Chemistry, vol. 71, No. 23, pp. 5354-5361, Dec. 1, 1999.
Partial European Search Report.
European Search Report.
EP Search Report, EP11167998.9, Mailed Sep. 26, 2011; Issued Sep. 15, 2011, Munich, Ex. Goers.
EP Search Report, EP11167999.9, Mailed Sep. 19, 2011; Issued Sep. 8, 2011, Munich, Ex. Goers.
EP Search Report, EP11168000.5, Mailed Sep. 19, 2011, Issued Sep. 8, 2011, Munich, Ex. Goers.
EP Search Report, EP11168002.1, Mailed Sep. 19, 2011, Issued Sep. 8, 2011, Munich, Ex. Goers.
EP Search Report, EP11168003.9, Mailed Sep. 19, 2011, Issued Sep. 8, 2011, Munich, Ex. Goers.
Tuval et al., "Neutrally Buoyant Particles and Bailout Embeddings in Three-Dimensional Flows," 5th International Summer School/Conference Proceedings, Let's Face Chaos Through Nonlinear Dynamics (online), Jun. 30-Jul. 14, 2002, Jul. 2002 (retrieved on Jan. 21, 2009). Retrieved from the Internet: http://www.camtp.uni-mb.si/chaos/2002/reports/abstracts.shtml.
Gascoyne et al., "Particle Separation by Dielectrophoresis," Electrophoresis 2002, 23, pp. 1973-1983, Houston, Texas, 2002.
Bennett et al., "Combined Field-Induces Dielectrophoresis and Phase Separation for Manipulating Particles in Microfluidics," American Institute of Physics, vol. 82, No. 23, pp. 4866-4868, Dec. 8, 2003.
Inglis et al., "Continuous Microfluidic Immunomagnetic Cell Separation," American Institute of Physics, vol. 85, No. 21, pp. 5093-5095, Nov. 22, 2004.
Giddings, "Field-Flow Fractionation: Analysis of Macromolecular, Colloidal, and Particulate Materials," Science, vol. 260, pp. 1456-1465, Jun. 4, 1993.
Reschiglian et al., "Field-Flow Fractionation and Biotechnology," TRENDS in Biotechnology, vol. 23, No. 9, pp. 475-483, Sep. 9, 2005.
Segré et al., "Radial Particle Displacements in Poiseuille Flow of Suspensions," Nature Publishing Group, No. 4760, pp. 209-210, Jan. 21, 1961.
Segré et al., "Behaviour of Macroscopic Rigid Spheres in Poiseuille. Flow Part 2. Experimental Results and Interpretation," Weizmann Institute of Schence, Rehovoth, Israel, pp. 136-157, received Nov. 6, 1961 and in revised form Mar. 16, 1962.
Leighton et al., "The Lift on a Small Sphere Touching a Plane in the Presence of a Simple Shear Flow," Journal of Applied Mathematice and Physics (ZAMP), vol. 36, pp. 174-178, Jan. 1985.
Cherukat et al., "The Inertial Lift on a Rigid Sphere in a Linear Shear Flow Field Near a Flat Wall," J. Fluid Mech. 1994, vol. 263, pp. 1-18, Received Mar. 8, 1993 and in revised form Aug. 18, 1993.
Saffman, "The Loft on a Small Sphere in a Slow Shear Flow," J. Fluid Mech. 1965, vol. 22, Part 2, pp. 385-400, Received Oct. 29, 1964.
Rubinow et al., "The Transverse Force on a Spinning Sphere Moving in a Viscous Fluid," Institute of Mathematical Sciences, New York University, New York, pp. 447-459, Mar. 13, 1961.
Ho et al., "Inertial Migration of Rigid Spheres in two-Dimensional Unidirectional Flows," J. Fluid Mech. 1974, vol. 65, Part 2, pp. 365-400, Received Sep. 4, 1973.
Vasseur et al., "The Lateral Migration of a Spherical Particle in Two-Dimensional Shear Flows," J. Fluid Mech. 1976, vol. 78, Part 2, pp. 385-413, Received Dec. 4, 1975.
Feng et al., "Direct Simulation of Initial Value Problems for the Motion of Solid Bodies in a Newtonian Fluid. Part 2., Couette and Poiseuille Flows," J. Fluid Mech. 1994, vol. 277, pp. 271-301, Received Sep. 20, 1993 and in revised form May 11, 1994.
Asmolov, "The Inertial Lift on a Spherical Particle in a Plane Poiseuille Flow at Large Channel Reynolds Number," J. Fluid Mech. 1999, vol. 381, pp. 63-87, Received Feb. 28, 1997 and in revised form Sep. 10, 1998.
Asmolov, "The Inertial Lift on a Small Particle in a Weak-Shear Parabolic Flow," American Institute of Physics, vol. 14, No. 1, Jan. 2002.
Matas et al., "Inertial Migration of Rigid Spherical Particles in Poiseuille Flow," J. Fluid Mech. 2004, vol. 515, pp. 171-195, Received Apr. 17, 2003 and in revised form Apr. 19, 2004).
Yang et al., "Migration of a Sphere in Tube Flow," J. Fluid Mech. 2005, vol. 540, pp. 109-131, Received Mar. 30, 2004 and in revised form Apr. 13, 2005.
Michaelides, Hydrodynamic Force and Heat/Mass Transfer From Particles, Bubbles, and Drops-The Freeman Scholar Lecture, Journal of Fluids Engineering, vol. 125, pp. 209-238, Mar. 2003.
Cherukat et al., "Wall-Induced Lift on a Sphere," Int. J. Multiphase Flow, vol. 16, No. 5, 1990, pp. 899-907, Received Nov. 6, 1989 and in revised form Apr. 1, 1990).
Cherukat et al., "The Inertial Lift on a Rigid sphere Translating in a Linear Shear Flow Field," Int. J. Multiphase Flow, vol. 20, No. 2, 1994, pp. 339-353, Received Feb. 20, 1993 and in revised form Oct. 10, 1993.
Berger et al., "Flow in Curved Pipes," Ann. Rev. Fluid Mech. 1983, vol. 15, pp. 461-512, 1983.
Gupalo et al., "Velocity Field of a Liquid Stream in a Spiral Channel of Rectangular Cross Section," pp. 109-112. Translated from Izvestiya Adademii Nauk SSSR, Mekhanika Zhidkosti I Gaza, No. 1, pp. 131-136, Jan.-Feb. 1977. Original article submitted Jan. 8, 1976.
Dean, "Fluid Motion in a Curved Channel," Imperial College of Science, pp. 402-420, Jul. 31, 1928.
Sudarsan et al., "Multivortex Micromixing," PNAS, vol. 103, No. 19, pp. 7228-7233, May 9, 2006.

(56) References Cited

OTHER PUBLICATIONS

Thiruvenkatachari et al., "Flocculation-cross-flow microfiltration hybrid system for natural organic matter (NOM) removal using hematite as a flocculent," Desalination, Elsevier, Amsterdam, NL, vol. 147, No. 1-3, XP 004386413, pp. 83-88, Sep. 10, 2002.

Xia et al., "Soft Lithography," Annu. Rev. Mater. Sci. 1998, vol. 28, pp. 153-184, 1998.

Sao et al., "Integrated Multiple Patch-Clamp Array Chip Via Lateral Cell Trapping Junctions," American Institute of Physics, vol. 84, No. 11, pp. 1973-1975, Mar. 15, 2004.

Ookawara et al., A Numerical Study of the Influenece of Particle Density on Lift Force-Induced Seperation in a Micro-Separator/Classifier by a Macroscopic Particle Model, Journal of Chemical Engineering of Japan, vol. 40, No. 11, pp. 986-992, 2007.

Ookawara et al., "Numerical study on development of particle concentration profiles in a curved microchannel," Chemical Engineering Science, 61, pp. 3714-3724, 2006.

* cited by examiner

PARTICLE SEPARATION AND CONCENTRATION SYSTEM

BACKGROUND

Particle separation and sorting are functions necessary in many biological and chemical processes for both macro-scale and miniaturized lab-on-chip applications. Some of the methods employed today are mechanical sieving and sedimentation—which are usually reserved for separation of large particles. Large scale water purification and mining/mineral recovery applications require large volume, high throughput, and rapid processing capabilities. Current water purification methods require sand beds and even membrane filters depending on the desired water quality. For example, mineral processing uses a spiral concentrator design where a helical trough allows heavy minerals to sediment near the center while centrifugal force pushes lighter particles outward where they are transported away. The tray has a sloped cross-section which is deeper near the axis of the helix.

Techniques such as hydrodynamic chromatography, size exclusion chromatography and electrophoresis allow separation of smaller particles. Most of these techniques have seen exponential growth but are batch processes that require set-up time for each sample lot. Field Flow Fractionation (FFF) is another macro-scale separation technique which is 30 years old but has attracted recent interest in microfluidics. This technique requires a transverse field which may be polarization, acoustic, magnetic, thermal, optical, or centrifugal, to sort and collect particles by elution. Particles are sorted by setting them at elevations that result in different flow velocity in the parabolic flow profile. Though the FFF technique is versatile and has the potential to be miniaturized, the requirement of an external field may increase the complexity of the device. Also, the use of a particular field method might limit its area of application to certain reagents (e.g. Magnetic FFF).

More recent developments in microfluidics based particle separation system include work reported by Yang et. al. (Yang S., Zhan J., Particle Separation in Microfluidic channels using flow control, Proceedings of IMECE04') based on the Zweifach-Fung effect, which involves passing the fluid through a channel bifurcation and maintaining different flow rates in each downstream daughter channel. Here the particles get moved into the daughter channel with the higher flow rate. Another approach is Pinched Flow Fractionation (PFF) (Takagi J., Yamada M., Yasuda M., Seki M., Continuous particle separation in a microchannel having asymmetrically arranged multiple branches, Lab on a chip 2005). In this method, the media and sample fluids are passed through a pinched section of a channel where the particles get aligned along the wall depending on their size and are subsequently separated downstream in the expansion region. Asymmetric Pinched Flow Fractionation (AsPFF) has also been carried out where the outlet channels have varying flow rates. This increases the resolution of the device. Continuous separation by the use of an asymmetric microfluidics cavity with a variable channel width along with modifying both flow rate and position of inlet of media and sample have been achieved by Zhang et. al. (Zhang X., Cooper J., Monaghan P., Haswell S., Continuous flow separation of particle within an asymmetric microfluidic device, Lab on a chip 2006). The phenomenon is based widely on 'pinched inlet' effect where the sample fluid and media fluid is passed side-by-side through a narrow section of the channel. Thus, the different sized particles are placed in different positions along the channel depending on their diameter. This section expands gradually and asymmetrically along the length and the particles, on the virtue of their initial position in the narrow section, get placed differentially downstream where the flow profile diverges and the separation thus amplifies owing to the laminar parabolic velocity profile. SPLITT Fractionation is another method used to separate and sort particles (Narayanan N., Saldanha A., Gale B., A microfabricated electrical SPLITT system, Lab on a chip 2005), which essentially utilize compression of the sample flow stream by media flow stream right at the inlet. The separation is achieved downstream. Ultrasonic particle separation is another way in which particles get arranged along a pressure node in the fluidic channel on the application of an acoustic field across the channel width (Kapishnikov S., Kantsler V., Steinberg V., Continuous particle size separation and size sorting using ultrasound in a microchannel, J. Stat. Mech. (2006) P01012). The particles can be collected downstream and separated from the flow by carefully modifying the downstream geometry. Size based separation may also be possible with this method by use of serpentine channels with the extractions ports as specific intervals. Microfluidics based centrifugal separation has been reported by Brenner (Brenner T., Polymer Fabrication and Microfluidic Unit Operations for Medical Diagnostics on a Rotating Disk, Dissertation at Institute of Microsystems, University of Frieburg, December 2005). This essentially is a miniature centrifuge constructed on a rotating disk with polymer microstructures to carry the fluid. Finally, Ookawara (Ookawara, S., Higashi, R., Street, D., and Ogawa, K. Feasibility Study on Concentrator of Slurry and Classification of Contained Particles by Micro-Channel, Chem. Eng. J., v. 101, 171-178 (2004)) reported on the use of 200 µm×170 µm microchannels with semicircular radius of 2 mm for centrifugal separation where slurry particles are directed into one arm of a bifurcation channel. The rectangular (170 µm×200 µm) cross-section leads to Dean's vortices in the transverse plane which enhance mixing and re-dispersion.

Difficulties with these types of implementations have been experienced, however. For example, all of these approaches require an additional external force, are limited to batch processing and are scaled only to handle small volumes of a sample.

Another important application of particle separation is bio defense—where the challenge is to determine and detect biological threats in the water supply. The DoD has set standards for expected limit of detection (LOD) for a list of potential agents. In particular, the Tri-Service Standard for anthrax spores is 100 cfus/L, which poses a significant challenge in logistics, time, and concentration factor. Neglecting all losses, at least 1000 L of water must be screened with a concentration factor of $10^6$ for a typical detector sensitivity of $10^5$ cfus/mL. The most popular method for screening large volumes of water is tangential flow filtration (TFF) with low molecular weight cut-off (MWCO) membranes (typically 30 KDa). The biggest challenge to this method and to all these vendors is the low yield and laborious back-flush recovery of captured pathogens from these membranes.

BRIEF DESCRIPTION

In one aspect of the presently described embodiments, the device comprises an inlet operative to receive fluid containing particles, a channel operative to allow a flow of the fluid, the channel being in a spiral configuration, a means for separating the particles within the fluid, and, at least one outlet for the fluid.

In another aspect of the presently described embodiments, the channel has a width, a height and a radius of curvature.

In another aspect of the presently described embodiments, the particles are separated based on at least one of the width, the height, the radius of curvature, a velocity of the fluid and a viscosity of the fluid.

In another aspect of the presently described embodiments, the width of the channel varies along the spiral.

In another aspect of the presently described embodiments, the means for separating comprises at least one cavity disposed along the channel.

In another aspect of the presently described embodiments, the means for separating comprises separated paths along the channel connected to corresponding outlets.

In another aspect of the presently described embodiments, the radius of curvature increases along the channel.

In another aspect of the presently described embodiments, the radius of curvature decreases along the channel.

In another aspect of the presently described embodiments, planar channels may be stacked into helical structures to expand for length within a constrained area or footprint.

In another aspect of the presently described embodiments, the inlet is operative to receive the fluid having particles from a pump.

In another aspect of the presently described embodiments, the outlet is operative to convey the fluid to a flow fractionation system.

In another aspect of the presently described embodiments, the at least one cavity includes a collar operative to be selectively rotated to one of an opened and closed position.

In another aspect of the presently described embodiments, the device further comprises at least one booster positioned in the channel.

In another aspect of the presently described embodiments, the booster is a hydrofoil.

In another aspect of the presently described embodiments, the spiral configuration comprises a first spiral portion and a second spiral portion.

In another aspect of the presently described embodiments, the first spiral portion includes the inlet disposed in a center thereof.

In another aspect of the presently described embodiments, the second spiral portion includes the outlet disposed in a center thereof.

In another aspect of the presently described embodiments, the first spiral portion is operative as a concentrator to compress particles against one side of the channel and the second spiral portion is operative as a separator to move particles across the channel.

In another aspect of the presently described embodiments, the inlet and the outlet are disposed on a periphery of the spiral configuration.

In another aspect of the presently described embodiments, the channel comprises a trough having a first depth on an outer wall of the spiral configuration and a second depth on an inner wall of the spiral configuration, the first depth being greater than the second depth.

In another aspect of the presently described embodiments, the method comprises forming a substrate having at least one channel formed therein, providing a first structure to a first end of the substrate, providing a second structure to a second end of the substrate, the second structure being operative as an outlet for the device, and, rolling the substrate around the first structure.

In another aspect of the presently described embodiments, the method further comprises laminating a second substrate to the substrate.

In another aspect of the presently described embodiments, the first structure is connected to the substrate and is operative as an inlet for the device.

In another aspect of the presently described embodiments, the first structure is operative to be removed from the device after the rolling.

DETAILED DESCRIPTION

Systems according to the presently described embodiments utilize channel geometry and velocity to exert the required force to separate particles to outside or inside channel walls. These embodiments may span micro-scale to macro-scale fluid capacities. Thus, many forms are possible, allowing parallelization or extended channel lengths through helical stacking of planar structures. As an additional advantage, materials and fabrication cost are also very low, thus allowing for disposable use.

Figure 1:
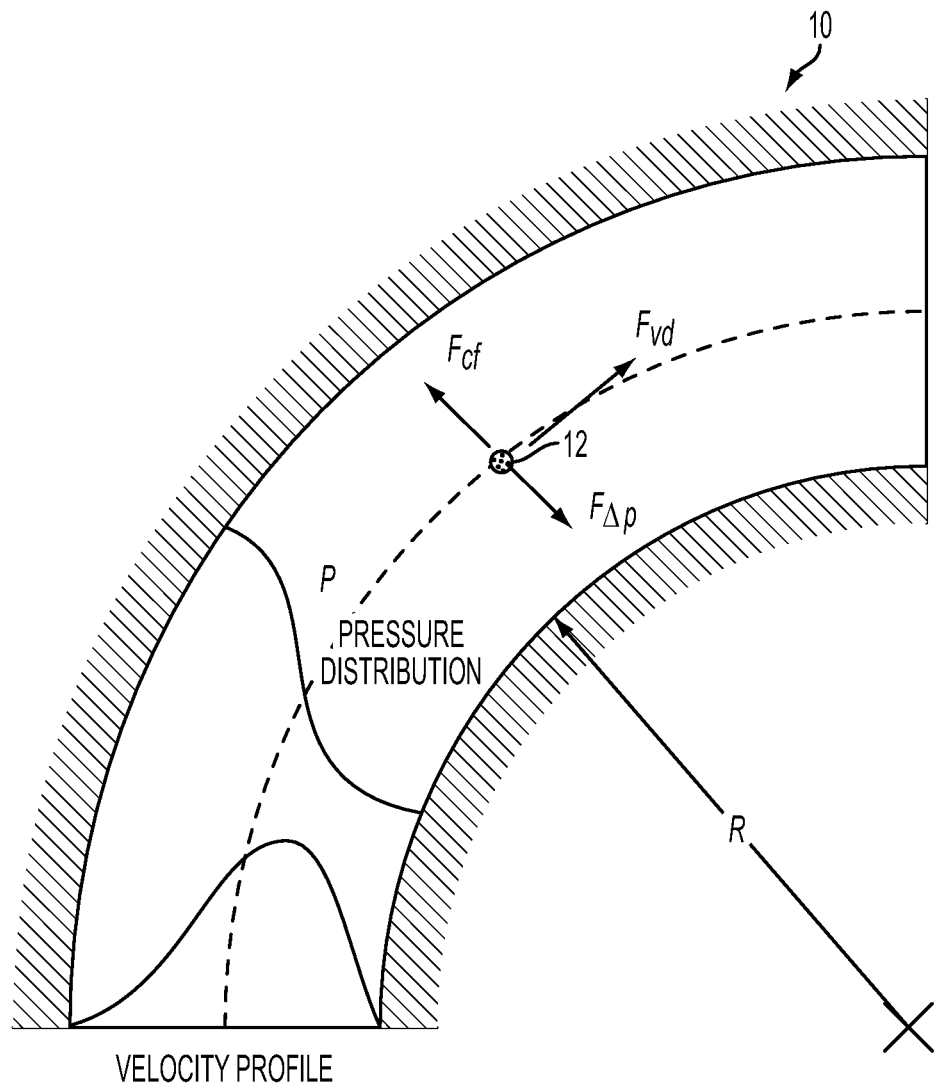
FIG. 1 is a graphic illustration of a fluid channel.

With reference to FIG. 1, a segment of a curved channel 10 showing various forces acting on a particle 12. Also, the velocity profile and the pressure distribution is shown.

Analytic consideration for the flow in a curved channel is as follows. In this regard:

V=Flow velocity
p=Pressure
$F_{cf}$=Centrifugal force on the particle
$F_{\Delta p}$=Force due to pressure differential
$F_{vd}$=Force due to viscous drag
R=Radius of curvature of the channel
η=Dynamic viscosity of the fluid
m=Mass of the particle
r=Radius of the particle assumed to be spherical
ρ=Density of fluid The expressions for the centrifugal ($\propto r^3$), transverse pressure driven ($\propto r^2$), and viscous drag forces ($\propto r$) acting on the particle can be expressed as follows:

$$F_{cf} = \frac{mV_\theta^2}{R} = \rho \frac{4}{3}\pi r^3 \frac{V_\theta^2}{R}$$

$$F_{\Delta p} = p\pi r^2$$

$$F_{vd} = 6\pi \eta r V_r$$

The particles will move outwards if $F_{cf} > F_{\Delta p}$, or $$\rho \frac{4}{3}\pi r^3 \frac{V_\theta^2}{R} > p\pi r^2 \quad (1)$$

i.e.

$$r > \frac{p}{\rho} \frac{R}{V_\theta^2} \frac{3}{4}$$

Equation (1) can be used to determine the lower bound for particle size that will move outwards for any given geometry, pressure and velocity of flow. Particles smaller than this lower bound will move inwards
or $$r < \frac{p}{\rho} \frac{R}{V_\theta^2} \frac{3}{4}$$

The distance of travel before particle migrates across the flow channel (transverse direction) is dependent on the relative magnitudes of $F_{vd}$ and $F_{\Delta p}$.

Also since $F_{\Delta p} \propto r^2$ and $F_{vd} \propto r$, larger particles will be more affected by the flow induced transverse pressure drop directed towards the inner surface.

The transverse pressure may be derived by considering peripheral flow in a concentric cavity where the parabolic profile fits:

$$V_\theta = V_0(r-r_1)(r_2-r)$$

and $r_1$ and $r_2$ are the inner and outer radii, respectively. The radial Pressure drop, p, is given by:

$$p = \int_1^2 \frac{\rho V_\theta^2}{R} dr =$$

$$V_0^2 \frac{\rho}{R} \left[ \frac{r^2}{5} - \frac{(r_1+r_2)r^4}{2} + \frac{r_1^2 + 4r_1 r_2 + r_2^2)r^3}{3} - r_1 r_2 (r_1+r_2)r^2 + r_1^2 r_2^2 r \right]$$

Figure 2A:
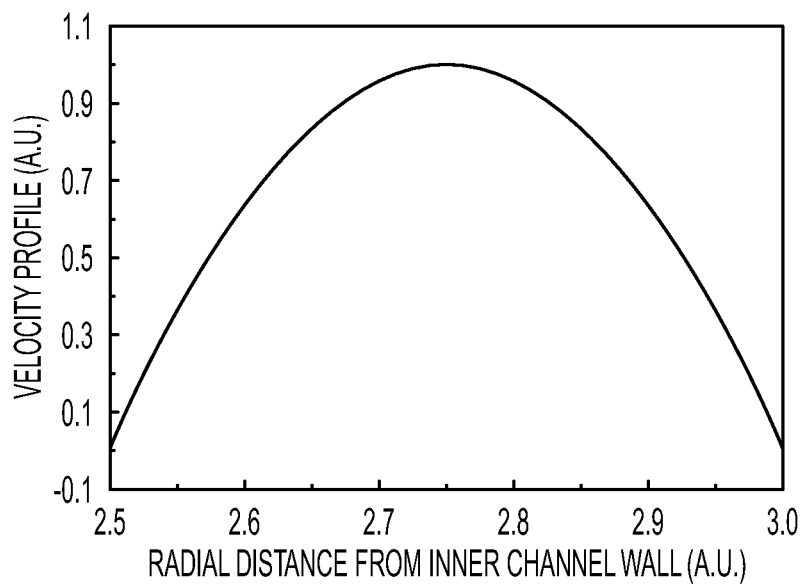
FIGS. 2(a) and 2(b) are graphs illustrating a velocity profile and a pressure profile.
Figure 2B:
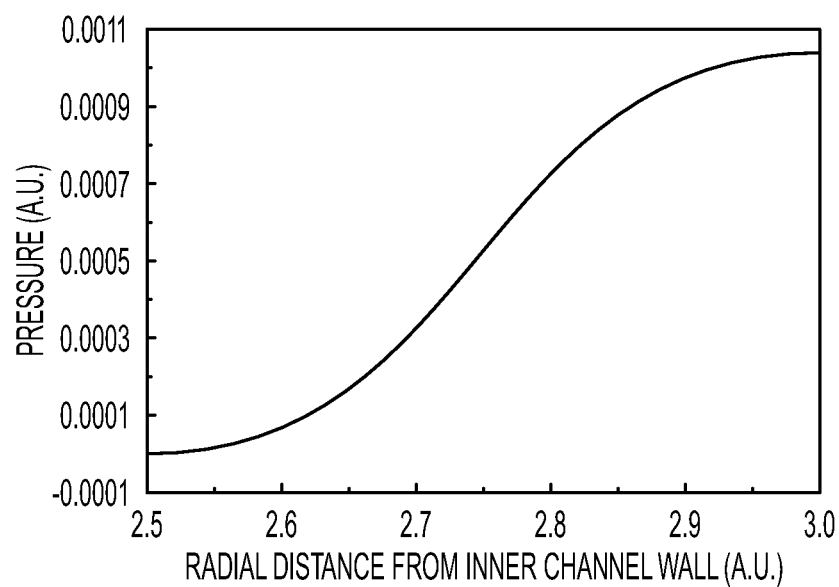

The calculated velocity and pressure profiles are shown in FIGS. 2(a) and 2(b). The pressure is displayed as a function of distance from the inner wall, beginning from $r_1$ and increasing to $r_2$. The inward-directed pressure field (from the outside wall) is clearly evident.

The required flow length of the channels is designed to meet the channel width and flow velocity for the particle size range. The equation of motion in the radial direction for outward directed motion is given by:

$$m \frac{dV_r}{dt} = \frac{mV_\theta^2}{R} - p\pi a^2 - 6\pi \eta a V_r = (\alpha - \beta V_r)m$$

where $$\alpha = \frac{V_\theta^2}{R} - \frac{p\pi a^2}{m}$$

$$\beta = \frac{6\pi \eta a}{m}$$

The solution to equation of motion is the radial velocity:

$$V_r = \frac{\alpha}{\beta}(1 - e^{-\beta t})$$

with acceleration time-constant, τ, given as:

$$\tau = \frac{1}{\beta} = \frac{m}{6\pi \eta a}$$

and terminal velocity of $$V_\infty = \frac{\alpha}{\beta}$$

The corresponding relationships for inward motion where transverse pressure is dominant and may be derived by changing the polarity of the centrifugal and pressure driven forces in the equation of motion.

This transit time has to be considered together with sedimentation time given by:

$$\tau_s = \frac{h}{V_y}$$

where h is channel height and $V_y$ is given by $$V_y = \frac{\gamma \frac{4}{3}\pi r^3 \rho_{particle} g}{6\pi \eta a}$$

and γ is the buoyancy term given by:

$$\gamma = \frac{\rho_{particle} - \rho_{fluid}}{\rho_{fluid}}$$

For particle separation, these relations are used to design a device for the desired particle size range. In this way, in one contemplated form of the presently described embodiments, a parallel array of collection outlets accumulate particles of the designed size range based on transit times and transverse migration velocities.

Figure 3:
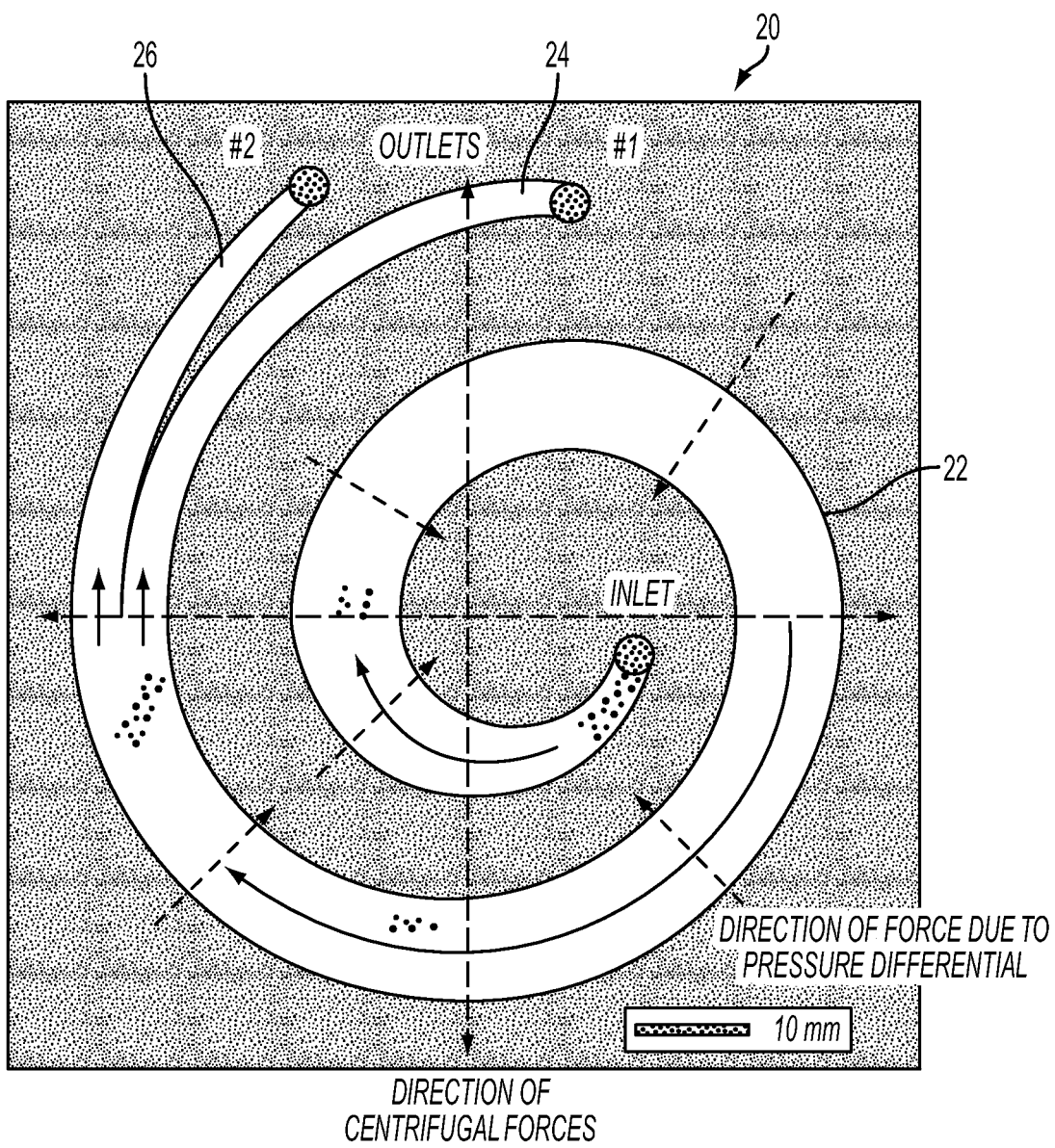
FIG. 3 is an illustration of one form of a fluid separation device according to the presently described embodiments.

In this regard, with reference now to FIG. 3, one form of a separation device 20 according to the presently described embodiments is shown. This form shows an expanding spiral channel 22 with increasing radius of curvature. This geometry takes advantage of the rate of pressure change: $dp/dR \propto 1/R^2$. In another form, the device may have a contracting spiral channel with decreasing radius of curvature for the side walls. In either case, the channel 22 evolves into two separate channels 24 and 26 (e.g., also referred to as channel #1 and channel #2 in the figures).

Figure 4:
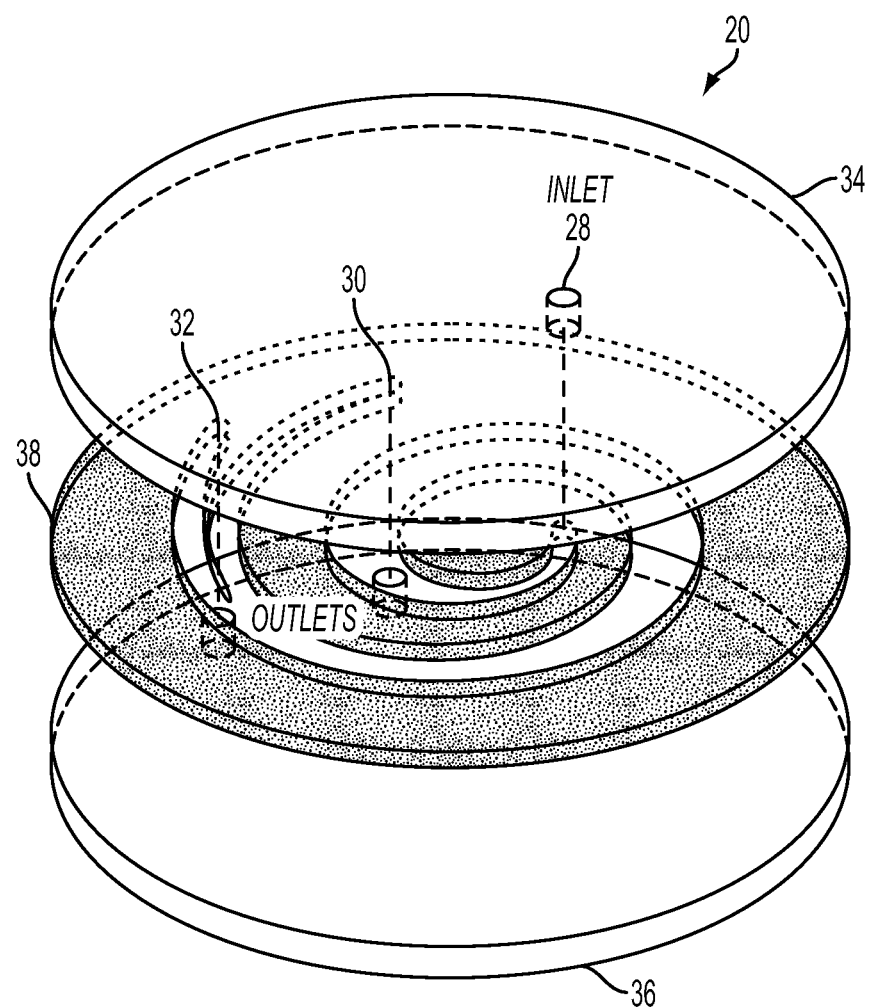
FIG. 4 is another illustration of the fluid separation device of FIG. 3.

An exploded view of the device 20 of FIG. 3 is shown in FIG. 4. In one form, the width of the widest section of the separation channel 22 is, for example, 10 mm and tapers to 5 mm near the inlet 28 and outlets 30, 32. The inlet 28 is near the center of the device 20 and the outlets 30, 32 are near the outer perimeter. Particles move with the fluid but also migrate across the channel cross-section. In one form, the height of the channel structure varies, for example, from 0.5 mm to 2 mm. Each outlet 30, 32 selectively collects separated particles depending on the fluidic velocity. Particles are collected in channel #1 (24) and #2 (26) at low and high fluid velocity, respectively.

The channels 22, 24 and 26 may be formed in a variety of manners, e.g., by cutting Acrylic sheets 34, 36 and 38 ($\frac{3}{16}$" and $\frac{1}{16}$" thickness) to the required dimensions using a laser cutter. The channels are then cut in the sheet 38. In one form, sheets 34 and 36 form the top and bottom covers and also provide holes for inlet 28 and outlet 30, 32. Although not shown, two 500 μm thick silicone sheets may form the fluidic seals at the two interfaces between the three Acrylic layers.

Notably, the presently described embodiments provide for particle separation in a variety of manners. For example, depending on the flow rate, the particle separation may be driven by the centrifugal force or the pressure that is created by the flow of fluid through the channel. In this regard, different outcomes result from the two different inlet flow rates. In either case, particle separation occurs.

Figure 5:
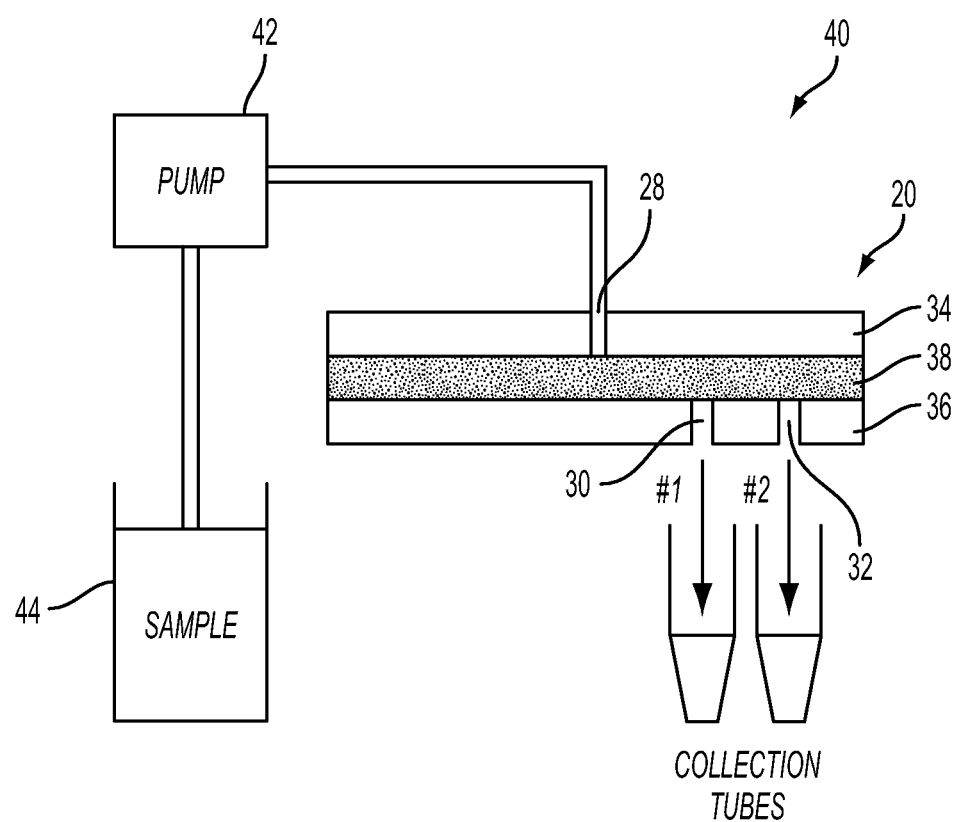
FIG. 5 is an illustration of a system incorporating the fluid separation device of FIG. 3.

At a flow rate of 50 mL/min (corresponding to approximately 1.75 cm/s nominal flow velocity) and with $\frac{3}{16}$" channel thickness, the force on the particle due to the pressure difference across the channel is more dominant compared to the centrifugal force experienced by the particles. This force is directed inwards towards the centroid of the radius of curvature. Thus, particles move towards the inner wall of the channel when they come across the spiral section. At the outlet fluidic junction, pushed particles follow an inner fluidic route and go out through the #1 outlet (as shown in FIG. 5). Particles used are FDA approved organic materials with a wide range of granularity.

At a flow rate of 62 mL/min (corresponding to approximately 5.25 cm/s nominal flow velocity) and with $\frac{1}{16}$" channel thickness, the centrifugal force on the particle dominates over the force due to the pressure gradient experienced by the particles. This force is directed outwards away from the centroid of the radius of curvature. Thus, the particles move towards the outer channel wall when they come across the spiral section. At the outlet fluidic junction, pushed particles follow an outer fluidic route and go out through the #2 outlet (as shown in FIG. 5).

With reference now back to FIG. 5, a system 40 includes the separation device 20 having an inlet 28 and outlets 30, 32. The fluid, or sample, 44, is provided to the inlet 28 through a pump 42. Also shown are collection tubes which correspond to the outlets 30, 32. It should be appreciated that the fluid that flows through the outlets into the collection tubes may also be provided to a variety of different systems for filtration and/or other fluid processing purposes.

Figure 6:
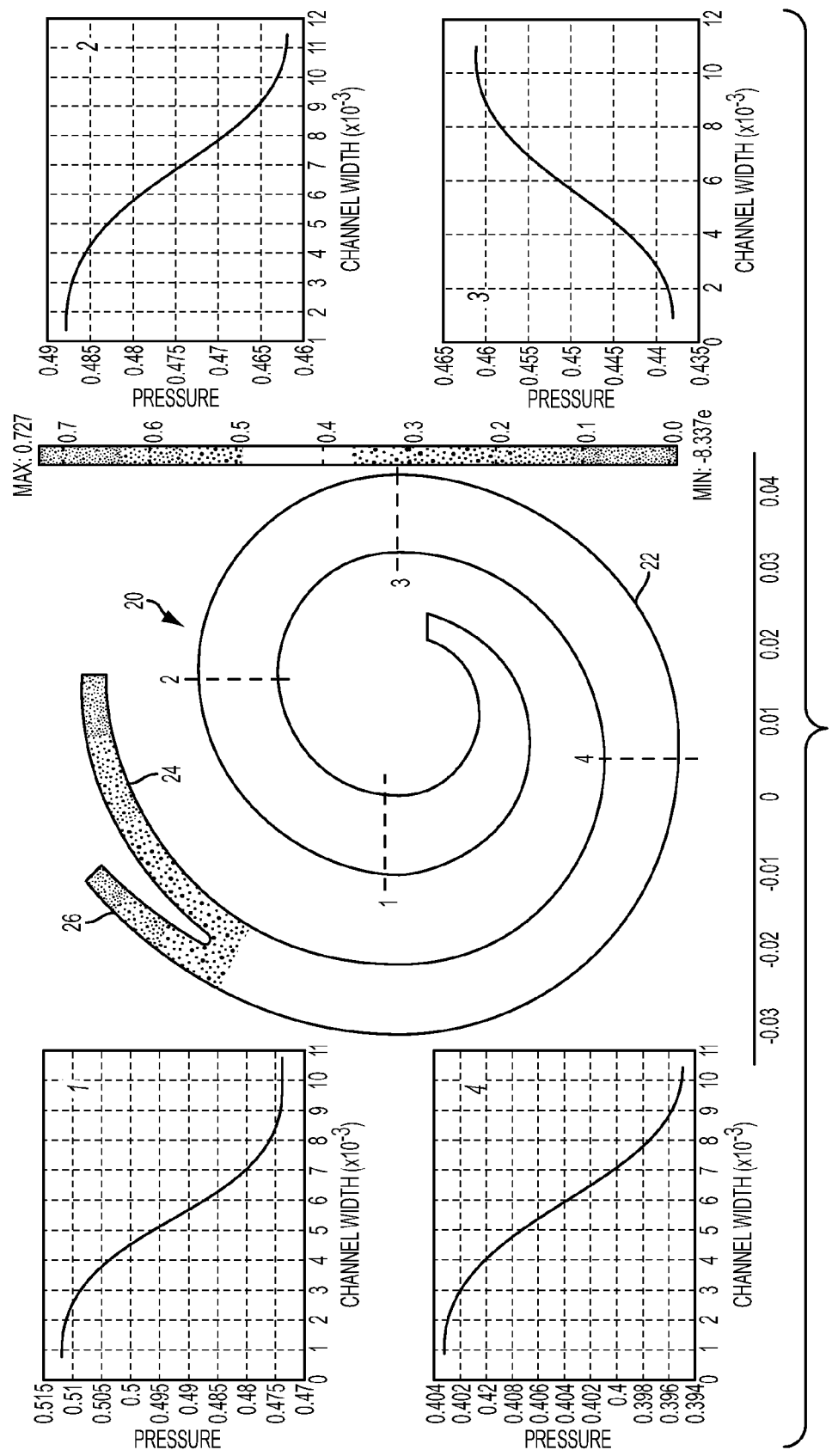
FIG. 6 is a representative view of a pressure profile of the fluid separation device of FIG. 3.

The flow solution for the spiral channel of FIG. 3 is simulated and shown in FIG. 6. The corresponding pressure distributions at the four orthogonal sections are also shown in FIG. 6. As shown, a large pressure gradient is found across the channel. In this regard, it will be appreciated that the pressure at the outer wall of the channel in each of the four cross section graphs (labeled 1, 2, 3, and 4) is greater than the pressure at the inner wall. This is apparent from these graphs, which plot pressure against channel width. In graphs 1, 2, and 4, the x-axis is a measure of channel width from the outer wall to the inner wall. In graph 3, the x-axis represents a measurement of channel width from the inner wall to the outer wall of the channel. Channel length may be designed for the range of particle sizes so that they are separated and collected by the two parallel collection outlets corresponding to paths 24 and 26. The number of collection outlets may be increased to narrow the range of particle sizes collected in each.

The spiraling effect of the channel results in a monotonic and continuous transverse separation force that moves particles transversely as a function of their size and as they move in the entrained flow field.

This implementation is intended to illustrate an operating embodiment. It is to be appreciated that various other combinations of dimension and flow rate may be selected for the relevant particle size range which will lead to micro-scale or macro-scale embodiments. Collection systems may be fluidic outlets or cavities.

Figure 7:
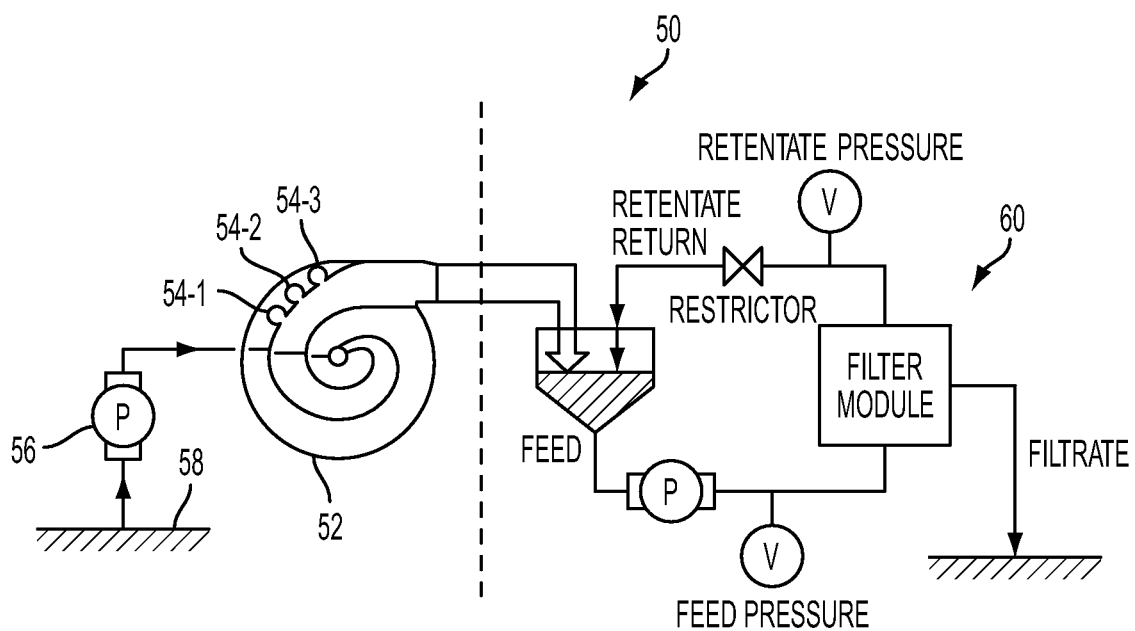
FIG. 7 is a representative view of a system incorporating a spiral concentrator upstream of a TFF system according to the presently described embodiments.

In another form of the presently described embodiments, a front-end to TFF for efficient and rapid screening of large volumes of water is shown in FIG. 7. A system 50 includes a coupled spiral concentrator 52 used as a front-end to a standard TFF system 60 for capturing particles of interest in the retentate. The system 60 is shown only in an exemplary form and may take a variety of other forms. Also shown are cavities 54-1, 54-2 and 54-3, as well as a pump 56 and sample 58. Larger particles (bacteria and parasites) are concentrated in the array of collection cavities while smaller particles (viruses, toxins, chemicals) are trapped in the TFF membrane or contained in the retentate. In this way, particulates above the designed cut-off value are removed from the fluid sample in the spiral concentrator 52 before it is fed to the TFF system. This minimizes the potential for clogging of the membranes that would require frequent cleaning. The spiral concentrator 52 uses a continuous process employing simple spiral channel geometry with fluidic velocity to achieve separation of particles over a large dynamic size range. As noted above, at high velocity, centrifugal force move particles to the outside wall where they accumulate and slide downstream.

Figure 8A:
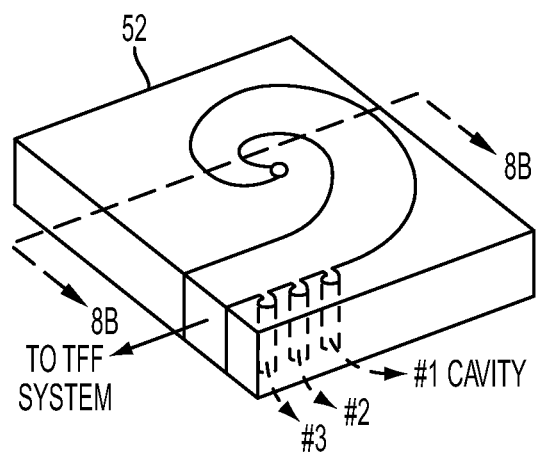
FIG. 8 is a perspective view of another form of a modular construction for a 2-piece spiral concentrator according to the presently described embodiments.
Figure 8B:
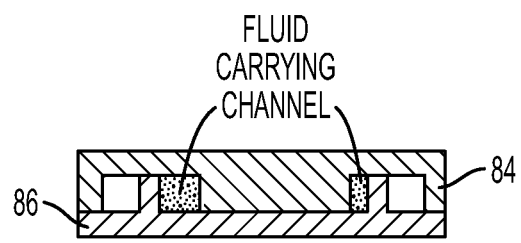

Referring now to FIG. 8, a modular two-piece top-bottom construction for a spiral concentrator, such as the spiral concentrator 52, is shown. It shows a perspective rendition of the spiral concentrator (left) and cross-sectional view (right) showing the desired flow channel given the combination of top and bottom plates 84 and 86. The footprint may be up to 12"×12" to maintain the centrifugal advantage and yet allow for several loops of the spiral channel with sizeable flow cross-sections. The top plate 84 can form fixed inside walls of the spiral channels. The lower plate 86 may have a range of radii for the outside walls of the spiral channels. Together, they form the desired flow cross-section.

Figure 9:
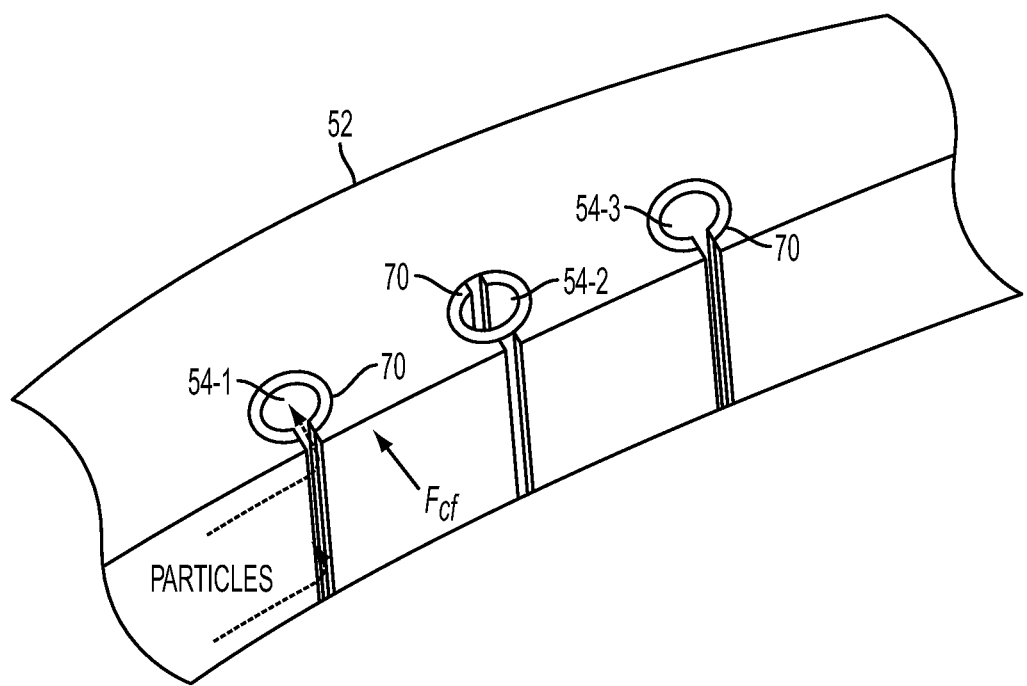
FIG. 9 is a view of the collection cavities on one or both sides of the spiral concentrator channel according to the presently described embodiments.

As shown in FIG. 9, at the end of the spiral channel, the array of collection cavities 54-1, 54-2 and 54-3 captures the particles. The cavities are designed to de-couple the flow field but allow access to the particles. Each cavity may have a slitted collar 70 that can rotate, by any appropriate technique, to "Open" or "Close" positions for concentrate collection and extraction, respectively. Of course, it will be understood that extraction can be accomplished in a variety of manners for this configuration and others disclosed herein. For example, a suitably sized pipette may be used to extract particles. For any particle size, the required channel dimension is determined by estimating the transit time to reach the side-wall. This time is a function of flow velocity, channel width, viscosity, and radius of curvature.

| Table of Parameters for High Volume Sample Processing with Spiral Concentrator ||||| 
|---|---|---|---|---|
| Flow Rate | Velocity | Dimension | Proc. Time | Volume |
| 62 mL/min | 5.25 cm/s | 10 × 1.6 mm | 16 min | 1 L |
| 3.6 L/min | 52.5 cm/s | 10 × 10 mm | 3 min | 10 L |
| 14.88 L/min | 52.5 cm/s | 10 × 40 mm | 6.7 min | 100 L |
| 74.4 L/min | 2.63 m/s | 10 × 40 mm | 13.4 min | 1000 L |
| 120 L/min | 2.5 m/s | 20 × 40 mm | 416.7 min | 50,000 L |
| 120 L/min | 2.5 m/s | 20 × 40 mm | 833.4 min | 100,000 L |

Some other operational parameters are tabulated above. Of particular significance is the projected parameters for high volumes that need to be screened for bio detection. The 120 L/min limitation to flow rate is the rating of the TFF membrane filters, which would be relaxed if particulates are removed using our spiral concentrator prior to introduction to the TFF system. Presently, membrane systems are not practical at these high volumes due to the low yield and laborious effort in recovery.

Figure 10A:
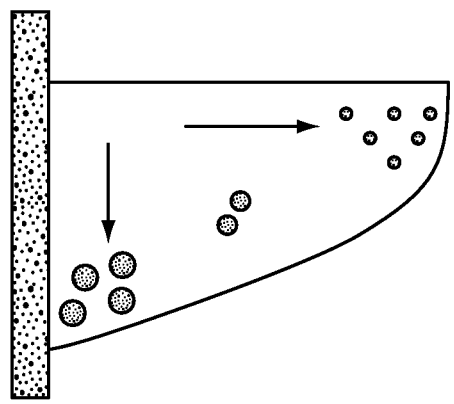
FIGS. 10(a) and 10(b) are cross-sectional views of a conventional spiral concentrator and a spiral concentrator according to the presently described embodiments, respectively.
Figure 10B:
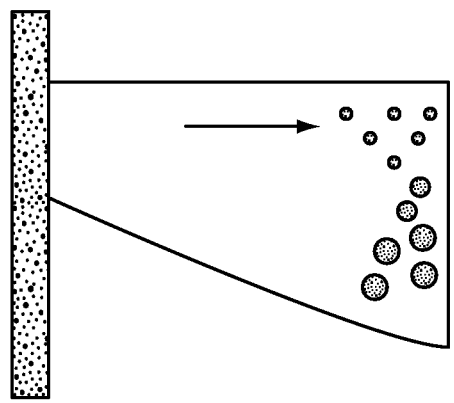

The typical flow cross-section of conventional spiral concentrators for mineral processing (as previously discussed) is an open trough with the heavy particles sedimenting out near the axis of a helix as shown in FIG. 10(*a*). The presently described embodiments include a modified enclosed trough where the increased depth further from the axis increases the volume of fluid (and therefore number of entrained particles) which will be subjected to centrifugal force in FIG. 10(*b*). In this way, all particles are moved outward for collection in the cavities or through outlets that may be provided to the helix.

The presently described embodiments solve the issue of an external field required for manipulating particles in the fluid. Particles can be separated from the fluid by the geometrical effect of the channel depending on the flow rate. Controlling the above parameters is easier compared to imposition of another transverse field as in FFF. Another advantage of this method is that continuous particle separation of a wide range of liquid volumes can be achieved. This is a great advantage when compared to techniques such as centrifugation or chromatography where real time particle collection cannot be possible.

As compared to other continuous particle separation processes, the advantage is the simplicity in geometric control of the device. In the continuous separation processes, which are based on Pinched Flow Fractionation, the sample flow stream has to be coupled with the media flow stream to decide the orientation of the particles, size wise, at the inlet section. The dimensions of this inlet section are comparable with the dimension of the particles. So precise control over the inlet section, where the pinched section lies, is required. The geometry of this section determines the separation trends downstream. Also, precise control of the flow rate of the media and sample are required. In the case of the presently described embodiments, geometric controls are only required on the channel width, height and the radius of curvatures of the curved sections. The channel widths need not be comparable with the size of the particle in question. The magnitude and the direction of the force on the particle can be manipulated just by changing these geometric parameters and the flow rate.

By easily altering the channel widths and the radius of curvatures of the curved sections, different size particles can be collected at different parallel outlets at the end of the spiral structure. The device can be scaled to separate particles sized below 10 μm. This is the typical range of biological samples.

The collection efficiency can be improved by, along with dimensional changes, the strategic placement of collection outlets. It will be appreciated that larger particles will be more affected by the flow induced transverse pressure drop directed towards the inner surface. The placement of a parallel array of collection chambers should result in better collection efficiencies. With appropriate considerations, collection chambers may also be placed sequentially along the spiral channel. This layout can easily be incorporated in the initial design.

A micro-scale version of such a device can be easily fabricated with simple techniques and can be easily integrated inline with other components in a Lab-on-chip type environment. The simplicity comes from the fact that a use of external field is eliminated. This makes the whole micro-scale analysis device much simpler and more reliable.

This invention also solves the issue of high volume, high throughput, rapid, screening of water and large scale processing of minerals. Particles can be separated from the fluid by the geometrical effect of the channel depending on the flow rate. Another advantage of this method is that continuous particle separation of a wide range of liquid volumes can be achieved. This is a great advantage when compared to techniques such as centrifugation or chromatography where real time particle collection cannot be possible.

The placement of an array of collection cavities sequentially along the spiral channel results in excellent collection efficiencies.

A micro-scale version of such a device can be easily fabricated with simple techniques and can be easily integrated inline with other components in a Lab-on-chip type environment.

The phenomenon is based on interplay of several forces acting on the particles in a curved section of the channel leading to a controllable resultant movement of the particles in the transverse direction. This phenomenon does not depend on any external field for particle manipulation. A continuous particle sorting functionality is possible depending on the device geometry and number of serpentine loops.

The device is planar with out of plane inlet and outlet. This makes it easier to stack several such devices together for parallel operation. The collection chambers can be accessed from the sides. The compactness and elimination of an external field makes it a very good candidate for Lab-on-chip type applications.

Different variations are possible along with the current design to suit a particular requirement. For example a spiral channel with converging or diverging cross section can be fabricated for better sorting of particles in different collection outlets. Moreover, the device is totally planer with out of plane inlet and outlet. This makes it easier to stack several devices on top of each other for parallel operation or as a single helical embodiment with longer looping (multi-turn) fluidic path such as those shown in FIG. 10(b). This device may also be miniaturized.

It should be understood that other variations of the presently described embodiments are contemplated and may be implemented in a variety of different environments. For example, with reference to FIG. 11, a spiral particle separation device 120 is illustrated. In this form, the device 120 includes an inlet 122 and an outlet 124 connected by a channel 126. Notably, the channel 126 is provided with a plurality of collection or trapping cavities, such as that shown at 128. These cavities may be spaced along the channel in any suitable manner. The cavities may also be sized to accommodate the objectives of the device. For example, the cavities may be configured to collect or trap particles of different sizes. In one example form, the channel is 1 mm wide while the spacing between the channels is 2 mm. Further, the cavity has an approximate diameter of 0.5 mm. The overall diameter of the device will vary based on the number of revolutions of the spiral channel; however, in one form, the overall diameter is 36 mm.

Figure 11:
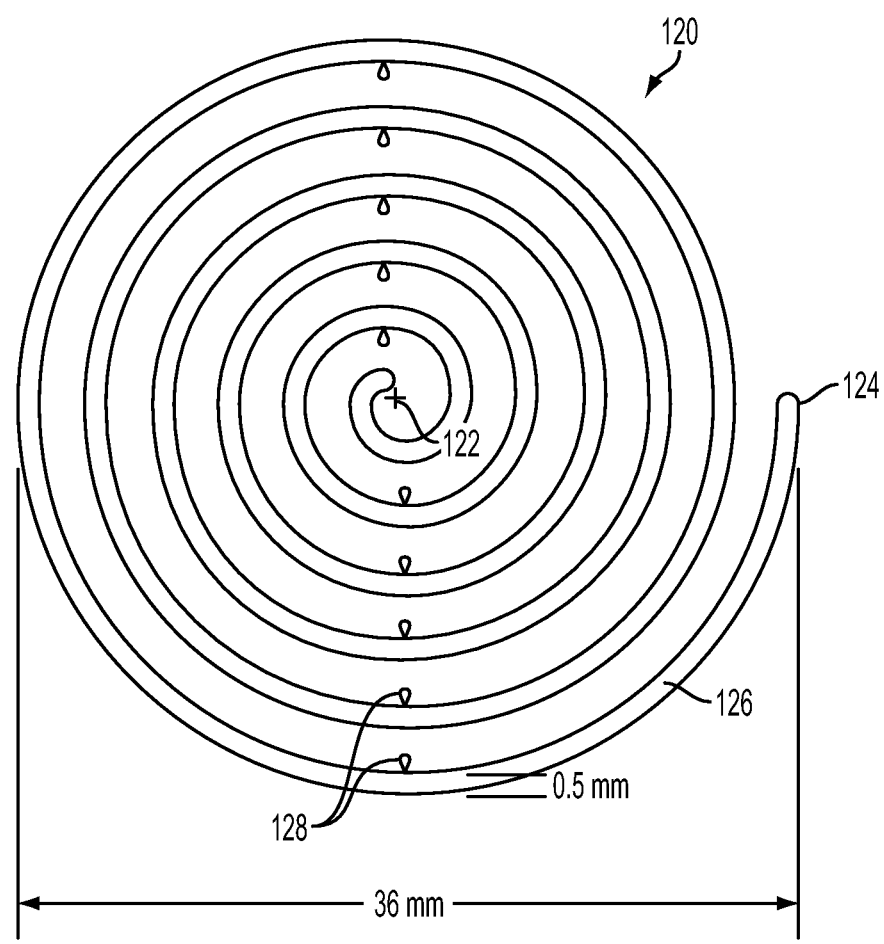
FIG. 11 is a representative view of another of the presently described embodiments.
Figure 12A:
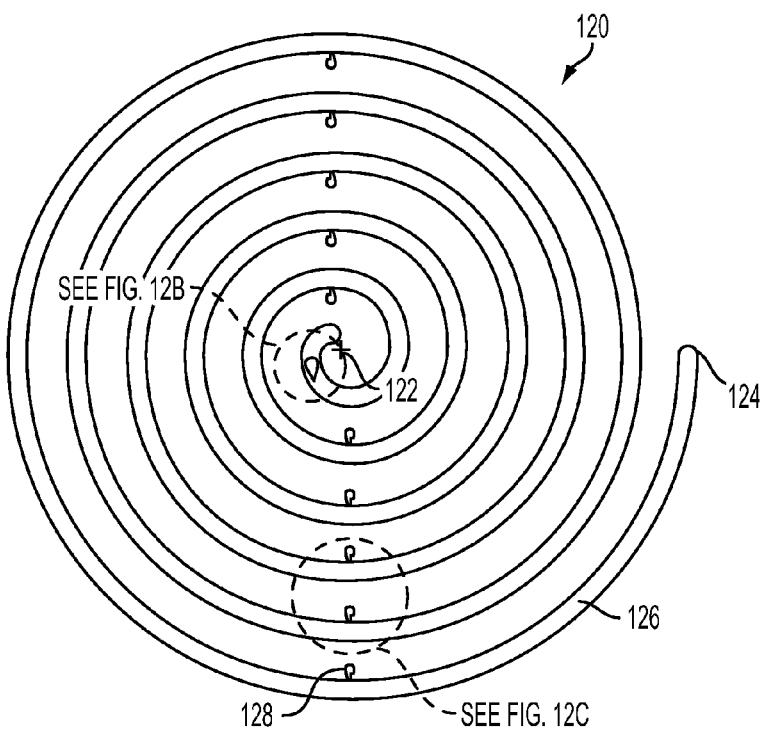
FIG. 12 is a representative view of another of the presently described embodiments.
Figure 12B:
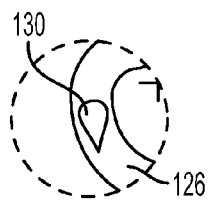
Figure 12C:
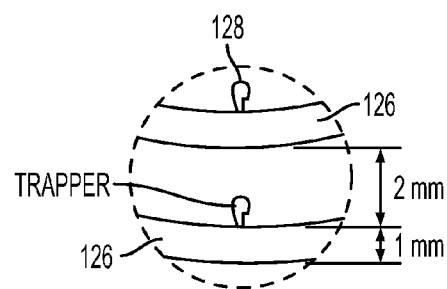

Referring now to FIG. 12, a variation of the embodiment of FIG. 11 is illustrated. In this regard, a booster 130 is disposed in the channel 126. The booster serves as an obstacle that allows for advantageous effects of a Bernoulli Effect on the fluid flow. In this configuration, the booster 130 narrows the separation band.

Figure 13:
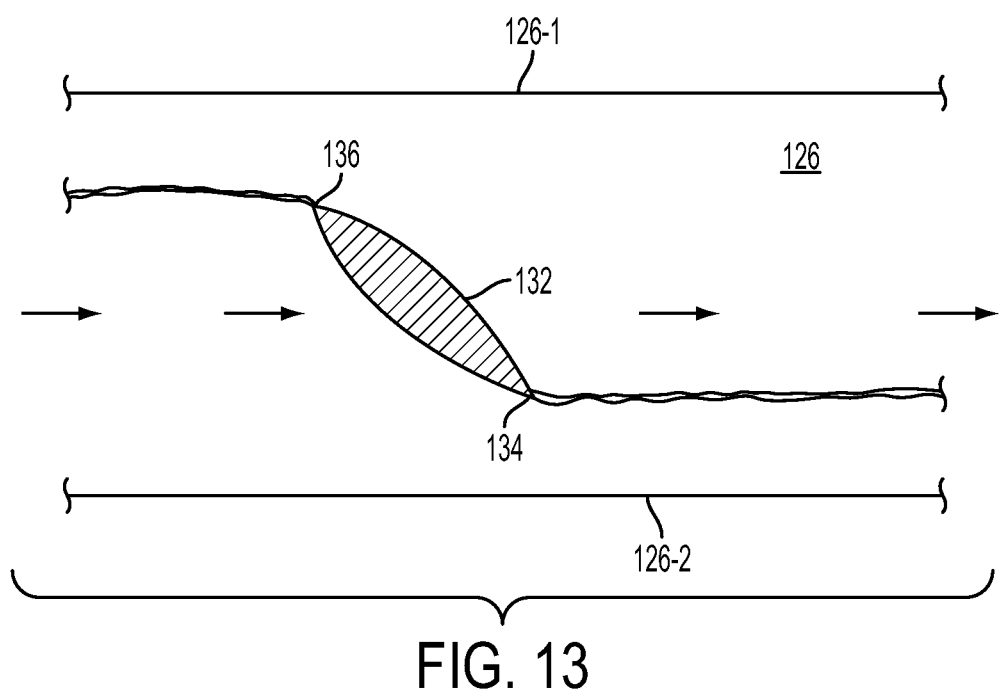
FIG. 13 is a representative view of another of the presently described embodiments.

A still further variation is illustrated in FIG. 13. The advantages of the Bernoulli Effect are realized here as well. As shown, the channel 126 is defined by an outer wall 126-1 and an inner wall 126-2. A booster, or hydrofoil, 132 is positioned in the channel such that a trailing edge 134 of the hydrofoil 132 is disposed closer to the inner wall 126-1 than the outer wall 126-2. The leading edge 136 is disposed closer to the outer wall 126-1 to create an angle of attack that results in a shortened flow path and transit time for collection of the particles coming off the trailing edge. Trapper cavities are located at 6 o'clock and 12 o'clock positions to collect separated particles of decreasing size range originating from the inlet.

Figure 14:
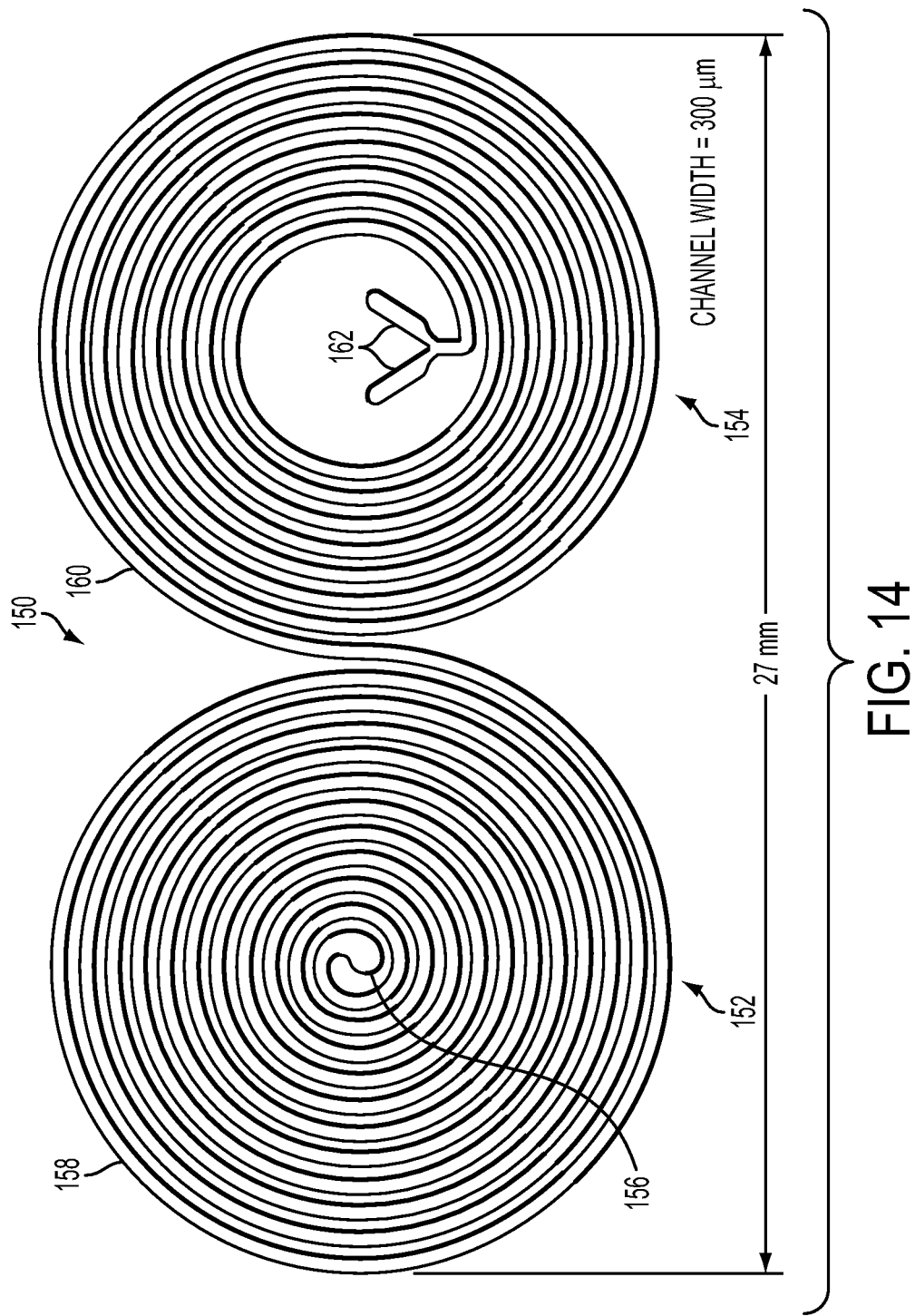
FIG. 14 is a representative view of another of the presently described embodiments.

A further embodiment is shown in FIG. 14. In this form, a separation device 150 includes two distinct but connected spiral portions 152 and 154 where the spiral portion 152 acts as the concentrator to compress particles against one wall and spiral portion 154 functions as the separator to move particles across the channel width. The compression of the mixture of particles into a narrow and tight band allows for increased separation resolution. Specifically, a mixture of particles in homogeneous distribution enters spiral portion 152 where the more dominant transverse force selected by the separation algorithm results in the migration of all particles towards the opposite inner (pressure driven force dominant) or outer wall (centrifugal force dominant). The separation along the flow path results from particles of different size and mass migrating at different rates. As shown, an inlet 156 is disposed in the center of spiral portion 152. The inlet allows for fluid to be introduced to a channel 158 of the device. The channel 158 connects to channel 160 of the spiral portion 154. The channel 160 spirals inward and terminates at outlet 162 in the spiral portion 154. This configuration allows for a device having advantageous dimensions (e.g. 27 mm long) without losing channel length.

Figure 15:
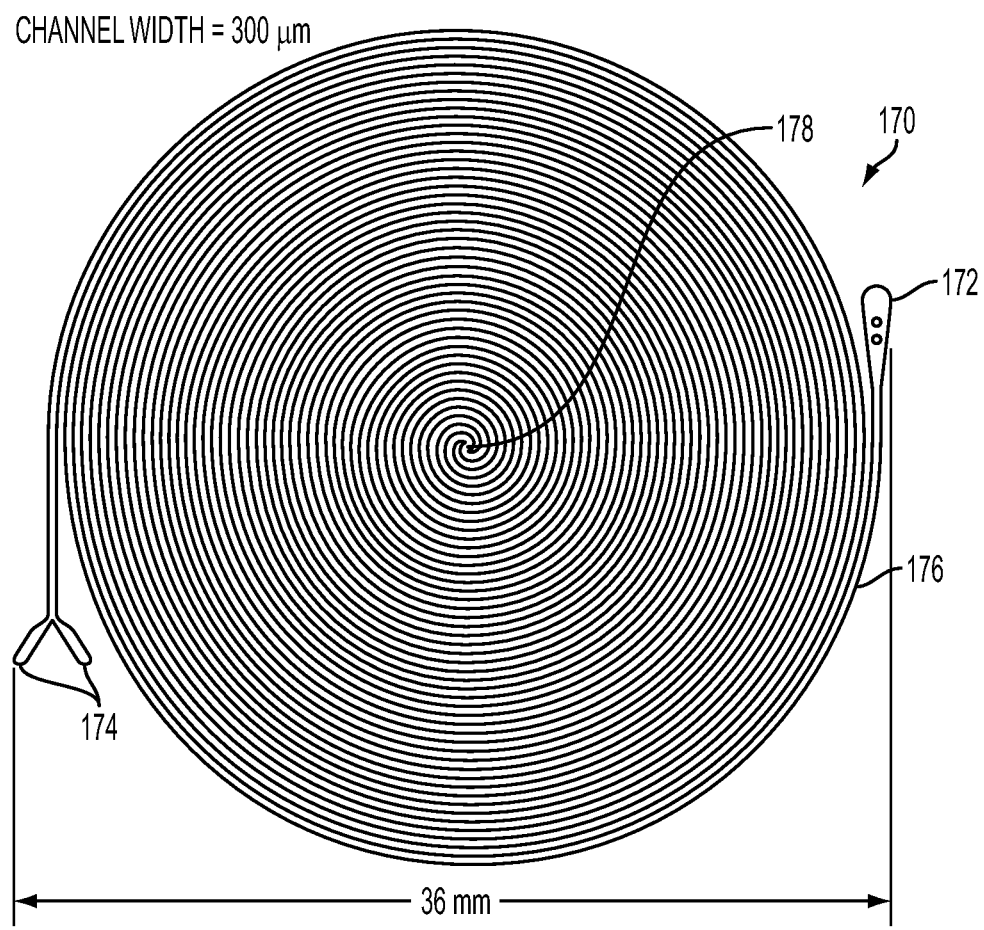
FIG. 15 is a representative view of another of the presently described embodiments.

With reference to FIG. 15, another embodiment is shown. In this embodiment, a spiral separation device 170 includes an inlet 172 that is disposed on the outer periphery of the device 170. An outlet 174 is likewise disposed on the periphery of the device 170. In this form, the inlet 172 is connected to the outlet 174 by a channel 176 that spirals inward to a center 178 (e.g. with a decreasing radius of curvature), then spirals outward to the outlet 174 (with an increasing radius of curvature). This embodiment allows for an efficient use of space, while maintaining sufficient channel length and achieving the sequential band compression and ensuing increased resolution in separation capability.

It should be appreciated that the channel width in any of these embodiments may be held constant along its length. The channel width may also be varied along its length. For example, the channel width may decrease along its length from the inlet to the outlet. Likewise, the width may increase along its length from the inlet to the outlet.

The embodiments described herein may be fabricated in a variety of manners. However, a convenient and scalable method of fabrication is shown in FIG. 16(a) through FIG. 16(g). This process includes the formation of a lamination and a roll-up thereof. The lamination may include a variety of different layers (e.g. 1, 2 or 3). The method is scalable. In this regard, the channel width defines a flow rate for the fluid while the channel length (i.e. the number of rotations) defines the efficiency of the device. In addition, an electric field can be added to the process for better efficiency.

Figure 16A:
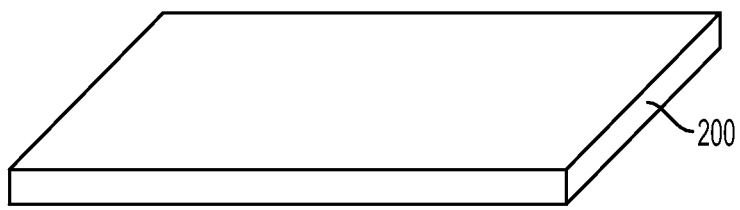
FIGS. 16(a)-(g) is a representative view of a method of fabrication according to the presently described embodiments; and, FIGS. 17(a)-(d) is a representative view of another method of fabrication according to the presently described embodiments.
Figure 16B:
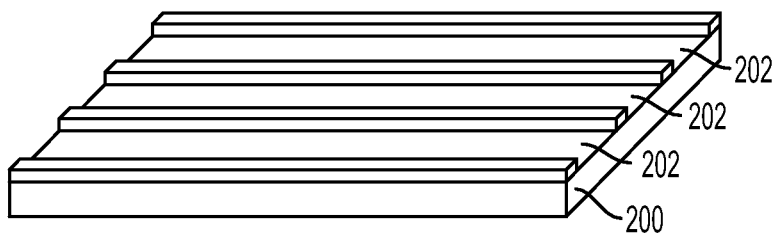
Figure 16C:
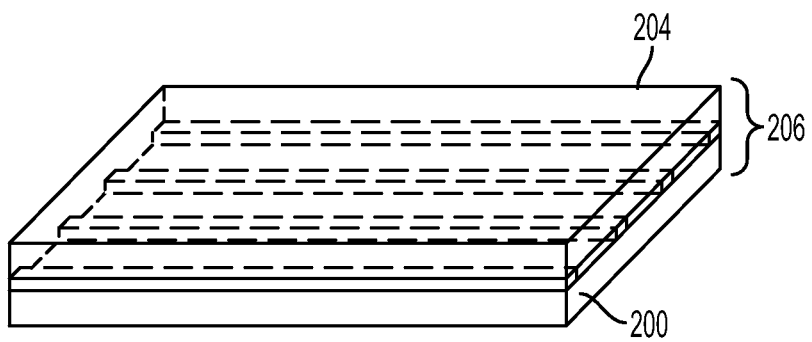
Figure 16D:
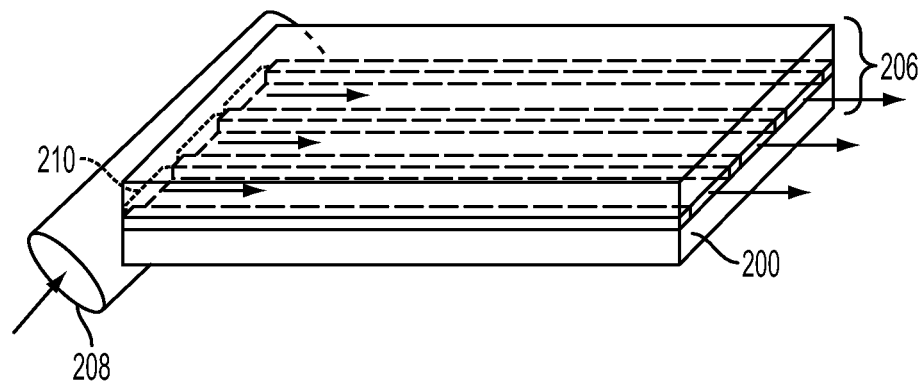
Figure 16E:
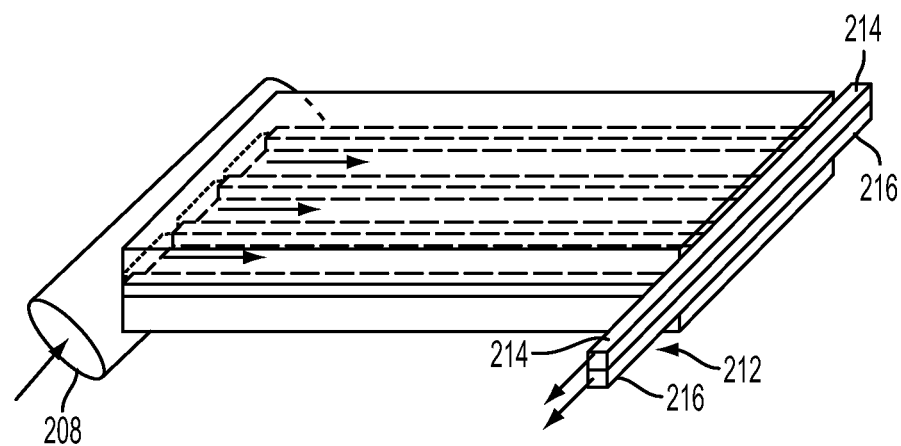
Figure 16F:
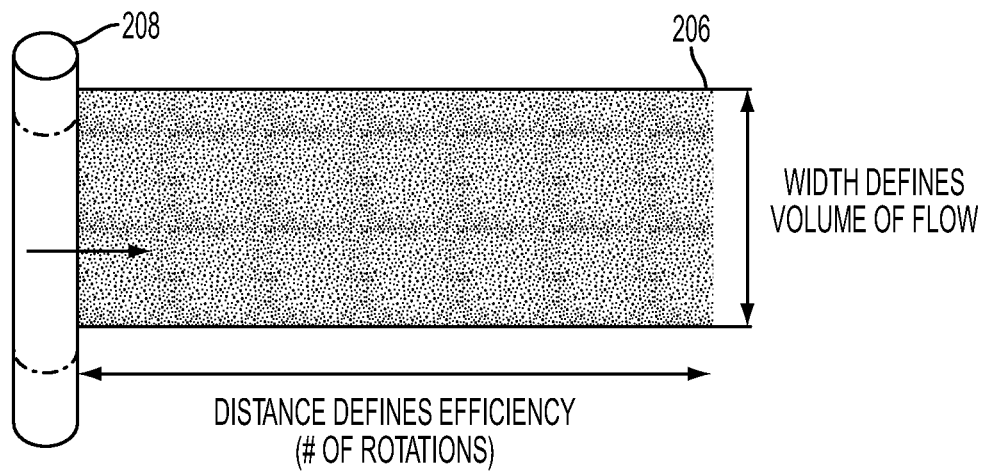
Figure 16G:
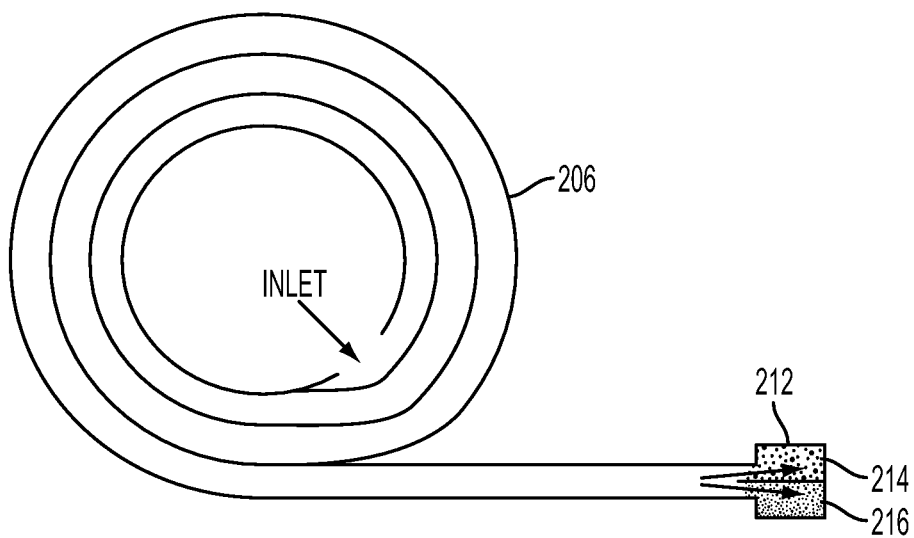
Figure 17A:
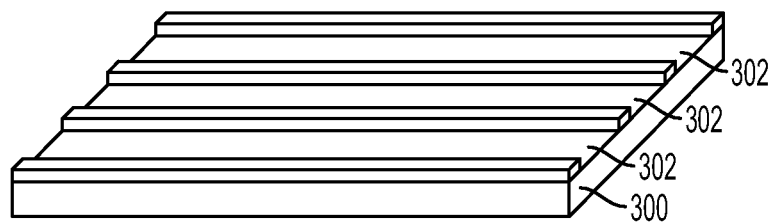
Figure 17B:
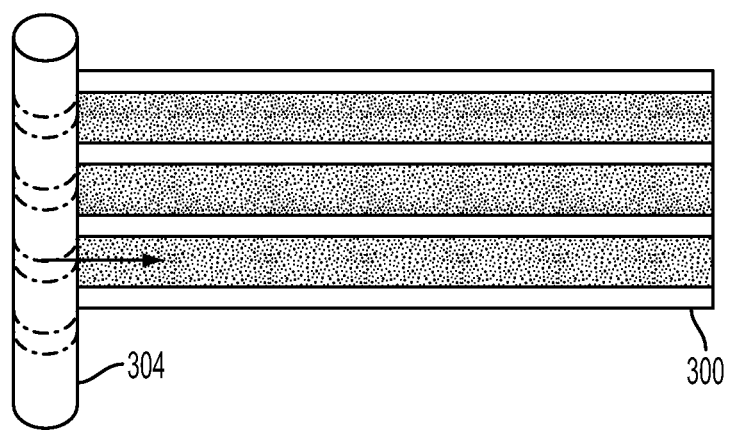
Figure 17C:
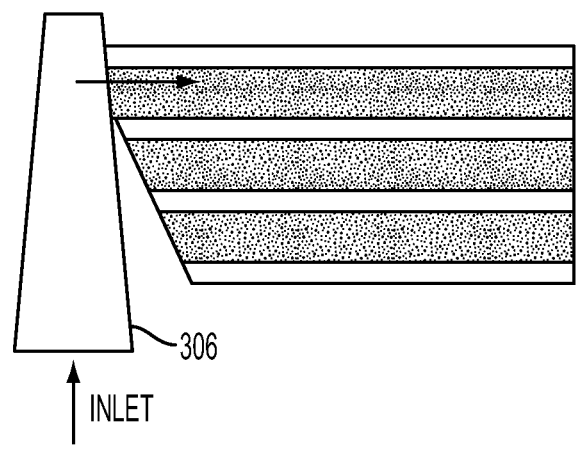
Figure 17D:
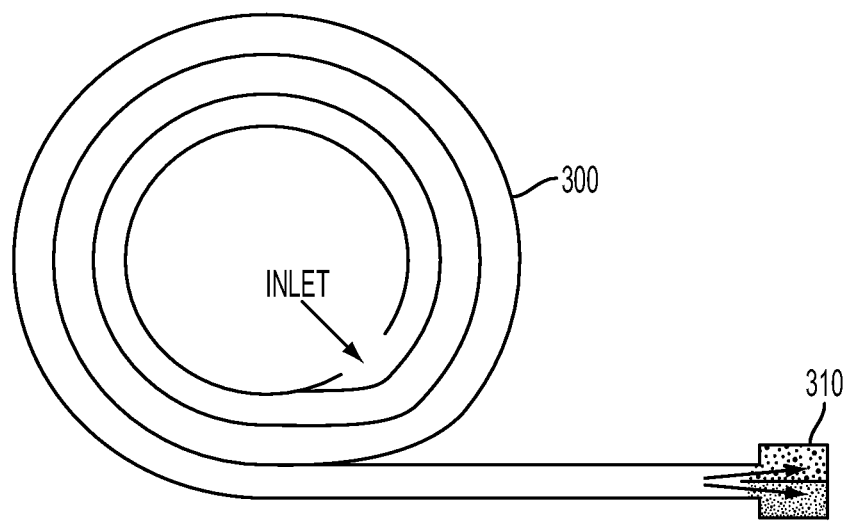

With reference to FIGS. 16(a)-(g), a flexible substrate 200 is initially provided (FIG. 16(a)). The substrate may be coated with an electrode and/or other surface treatment. Next, gap supports and channel separators are formed in the substrate to define the channels 202 (FIG. 16(b)). In this regard, grooves may be formed in the substrate itself or in an added layer. A second flexible substrate 204 is positioned over the defined channels 202 to form a lamination 206 (FIG. 16(c)). This substrate may likewise be coated with an electrode and/or other surface treatment. An inlet 208 is then connected to the lamination 206 (FIG. 16(d)). This inlet may take the form of a tube or rod that is perforated. Perforations 210 are aligned with the channels 202 to allow for fluid flow there-between. An outlet 212 is connected to an opposite end of the lamination 206 (FIG. 16(e)). The outlet 212 may take the form of tubes or rods that are perforated and provide of two separate outflows of fluid. Perforations (not shown) are aligned with the channels 202. It should also be understood that the each channel, in one form, is provided with two outlet perforations, one for a first outflow 214 and one for a second outflow 216. The lamination 206 is then rolled (FIG. 16(f)). In one form, the rolling is initiated at the inlet side of the lamination. A cross-section of the rolled device is shown in FIG. 16(g).

Another fabrication technique is illustrated in FIG. 17(a) through FIG. 17(d). Initially, a flexible substrate 300 is provided (FIG. 17(a)). The substrate 300 includes preformed channels 302. The channels 302 may be formed as an integral part of the substrate or may be formed as added or subtracted layers. A surface coating may also be applied to the substrate. Next, an inlet tube 304 is connected to the substrate (FIG. 17(b)). Perforations (not shown) in the tube 304 are aligned with the channels 302. In this form, the front side of the substrate laminates directly to the backside. There is no second substrate, as with the previous embodiment. As an alternative, an unconnected roll 306 may simply be used, the roll 306 being removed later (FIG. 17(c)). In this alternative, the front side of the substrate laminates to the backside. As shown, the inlet side of the substrate may be angled to even out any pressure drop. The formed device with an outlet 310 is shown in cross-section in FIG. 17(d).

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A device for handling particles within a fluid, the device comprising:
an inlet operative to receive fluid containing particles;
a channel operative to allow a flow of the fluid, the channel being in a spiral configuration to separate particles based on geometric parameters and by allowing a continuous flow of the fluid at a flow velocity to move particles through the channel and selectively migrate particles across the channel based on centrifugal forces and pressure driven forces to separate particles to outside or inside walls of the channel;
a means for collecting the particles within the fluid; and,
at least one outlet for the fluid.

2. The device as set forth in claim 1 wherein the channel has a width, a height and a radius of curvature.

3. The device as set forth in claim 2 wherein the particles are separated based on the geometric parameters comprising at least one of the width, the height, and the radius of curvature, the velocity of the fluid or a viscosity of the fluid.

4. The device as set forth in claim 2 wherein the width of the channel varies along the spiral.

5. The device as set forth in claim 1 wherein the means for collecting comprises at least one cavity disposed along the channel.

6. The device as set forth in claim 1 wherein the means for collecting comprises separated paths along the channel connected to corresponding outlets.

7. The device as set forth in claim 2 wherein the radius of curvature increases along the channel.

8. The device as set forth in claim 2 wherein the radius of curvature decreases along the channel.

9. The device as set forth in claim 2 wherein planar channels may be stacked into helical structures to expand for length within a constrained area or footprint.

10. The device as set forth in claim 1 wherein the inlet is operative to receive the fluid having particles from a pump.

11. The device as set forth in claim 1 wherein the outlet is operative to convey the fluid to a flow fractionation system.

12. The device as set forth in claim 5 wherein the at least one cavity includes a collar operative to be selectively rotated to one of an opened and a closed position.

13. The device as set forth in claim 1 further comprising at least one booster positioned in the channel.

14. The device as set forth in claim 13 wherein the booster is a hydrofoil.

15. The device as set forth in claim 1 wherein the spiral configuration comprises a first spiral portion and a second spiral portion.

16. The device as set forth in claim 15 wherein the first spiral portion includes the inlet disposed in a center thereof.

17. The device as set forth in claim 15 wherein the second spiral portion includes the outlet disposed in a center thereof.

18. The device as set forth in claim 15 wherein the first spiral portion is operative as a concentrator to compress particles against one side of the channel and the second spiral portion is operative as a separator to move particles across the channel.

19. The device as set forth in claim 15 wherein the inlet and the outlet are disposed on a periphery of the spiral configuration.

20. The device as set forth in claim 1 wherein the channel comprises a trough having a first depth on an outer wall of the spiral configuration and a second depth on an inner wall of the spiral configuration, the first depth being greater than the second depth.

21. A device for handling particles within a fluid, the device comprising:
an inlet operative to receive fluid containing particles;
a curved channel configured to separate particles based on geometric parameters and by allowing a continuous flow of the fluid at a flow velocity to move particles through the channel and selectively migrate particles across the channel based on centrifugal forces and pressure driven forces to separate particles to outside or inside walls of the channel; and,
at least one outlet for the separated particles.

22. The device as set forth in claim 21, wherein the geometric parameters comprise a width, a height and a radius of curvature of the channel, and wherein the particles are separated based on at least one of the width, the height, the radius of curvature, a velocity of the fluid and a viscosity of the fluid.

23. The device as set forth in claim 22, wherein the width of the channel varies along the curve.

24. The device as set forth in claim 22, wherein the radius of curvature either increases or decreases along the channel.

25. The device as set forth in claim 21, wherein the at least one outlet comprises at least two outlets.

26. The device as set forth in claim 21, wherein the channel comprises a trough having a first depth on an outer wall of the spiral configuration and a second depth on an inner wall of the spiral configuration, the first depth being greater than the second depth.

27. The device as set forth in claim 21, wherein the curved channel is a spiral.

28. A method for handling particles within a fluid, the method comprising:
receiving fluid containing particles at an inlet;
separating particles in a curved channel based on geometric parameters and by generating a continuous flow of the fluid at a flow velocity in the channel to move particles through the channel and selectively migrate particles across the channel based on centrifugal forces and pressure driven forces to separate particles to outside or inside walls of the channel; and
moving separated particles through an outlet.

29. The method as set forth in claim 28, wherein the geometric parameters comprise a width, a height and a radius of curvature of the channel, and wherein the particles are separated based on at least one of the width, the height, the radius of curvature, the flow velocity of the fluid and a viscosity of the fluid.

30. The method as set forth in claim 28, wherein the width of the channel varies along the curve.

31. The method as set forth in claim 28, wherein the radius of curvature either increases or decreases along the channel.

32. The method as set forth in claim 28, wherein the outlet comprises at least two outlets.

33. The method as set forth in claim 28, wherein generating the flow comprises controlling the flow velocity.

34. The method as set forth in claim 28, wherein the curved channel is a spiral.

\* \* \* \* \*